(12) United States Patent
Zoellner et al.

(10) Patent No.: US 11,987,784 B2
(45) Date of Patent: May 21, 2024

(54) SAMPLING SYSTEM AND METHOD OF USING THE SAME

(71) Applicant: SAINT-GOBAIN PERFORMANCE PLASTICS CORPORATION, Solon, OH (US)

(72) Inventors: Clemens E. Zoellner, Bay City, MI (US); Thomas R. Nixon, Au Gres, MI (US); Jonathon Wheatley, Midland, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 351 days.

(21) Appl. No.: 17/348,961

(22) Filed: Jun. 16, 2021

(65) Prior Publication Data

US 2021/0388304 A1 Dec. 16, 2021

Related U.S. Application Data

(60) Provisional application No. 63/039,848, filed on Jun. 16, 2020.

(51) Int. Cl.
*C12M 1/00* (2006.01)
*B01L 3/00* (2006.01)
(Continued)

(52) U.S. Cl.
CPC ........... *C12M 33/04* (2013.01); *B01L 3/0293* (2013.01); *B01L 3/502* (2013.01); *B01L 13/00* (2019.08);
(Continued)

(58) Field of Classification Search
None
See application file for complete search history.

(56) References Cited

U.S. PATENT DOCUMENTS

| | | |
|---|---|---|
| 6,293,163 B1 | 9/2001 | Johnston et al. |
| 7,052,603 B2 | 5/2006 | Schick |

(Continued)

FOREIGN PATENT DOCUMENTS

| | | |
|---|---|---|
| CN | 110129186 A | 8/2019 |
| WO | 03039961 A3 | 5/2003 |

(Continued)

OTHER PUBLICATIONS

International Search Report and Written Opinion for PCT/US2021/037553, dated Oct. 5, 2021, 12 pages.

*Primary Examiner* — Jyoti Nagpaul
(74) *Attorney, Agent, or Firm* — Abel Schillinger, LLP; Chi Suk Kim

(57) ABSTRACT

The present application is directed to a sampling system for sampling a fluid from a vessel, where the sampling system includes a sterile dispenser assembly operatively connected to the vessel, the sterile dispenser assembly including a valve operatively connected to the vessel, a membrane, and a needle, and a detachable sterile sampling container assembly operatively connected to the sterile dispenser assembly, the detachable sterile sampling container assembly including a sampling container, a membrane attached to the sampling container, and a sampling container housing enclosing the sampling container, where the sampling container housing includes a compressible portion having a deflated configuration and an expanded configuration.

19 Claims, 13 Drawing Sheets

(51) Int. Cl.
   *B01L 3/02*   (2006.01)
   *C12M 1/12*   (2006.01)
   *C12M 1/26*   (2006.01)
   *G01N 1/14*   (2006.01)

(52) U.S. Cl.
   CPC ............ *C12M 23/22* (2013.01); *C12M 23/28* (2013.01); *C12M 23/38* (2013.01); *C12M 37/00* (2013.01); *G01N 1/14* (2013.01); *B01L 2300/042* (2013.01); *B01L 2300/168* (2013.01); *B01L 2400/0406* (2013.01); *B01L 2400/06* (2013.01); *G01N 2001/1427* (2013.01)

(56) References Cited

U.S. PATENT DOCUMENTS

| | | |
|---|---|---|
| 7,578,205 B2 | 8/2009 | Belongia |
| 8,899,267 B2 | 12/2014 | Diodati et al. |
| 9,662,271 B2 * | 5/2017 | Holt .................. A61J 1/201 |
| 9,743,874 B2 | 8/2017 | Kashmirian |
| 2003/0069543 A1 | 4/2003 | Carpenter et al. |
| 2005/0107765 A1 | 5/2005 | Kashmiran et al. |
| 2007/0193376 A1 | 8/2007 | Sharma et al. |
| 2007/0227270 A1 | 10/2007 | Mennenga et al. |
| 2010/0326212 A1 | 12/2010 | Furey et al. |
| 2011/0241262 A1 | 10/2011 | Siddhamalli et al. |
| 2014/0073990 A1 | 3/2014 | Holmes et al. |
| 2014/0155782 A1 | 6/2014 | Bullington et al. |
| 2017/0362556 A1 | 12/2017 | Ali |
| 2018/0049947 A1 | 2/2018 | Brandenburger et al. |
| 2020/0146934 A1 | 5/2020 | Werth et al. |

FOREIGN PATENT DOCUMENTS

| | | |
|---|---|---|
| WO | 2011140596 A1 | 11/2011 |
| WO | 2020008067 A1 | 1/2020 |

* cited by examiner

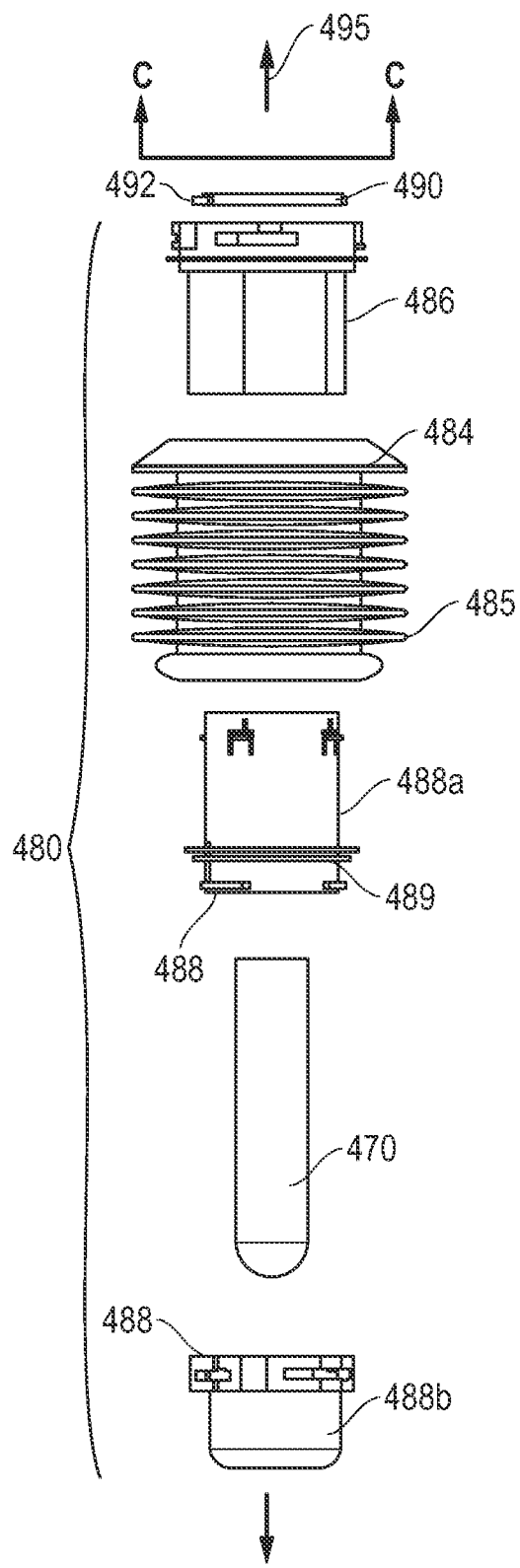
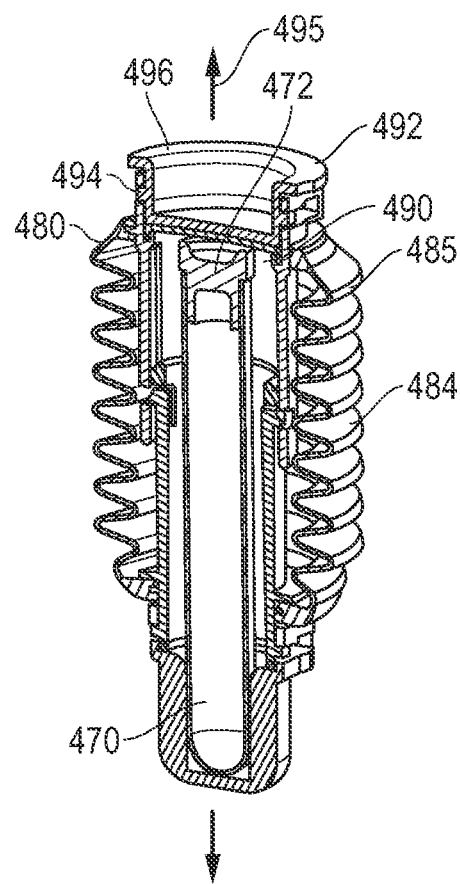
FIG. 4A
FIG. 4B

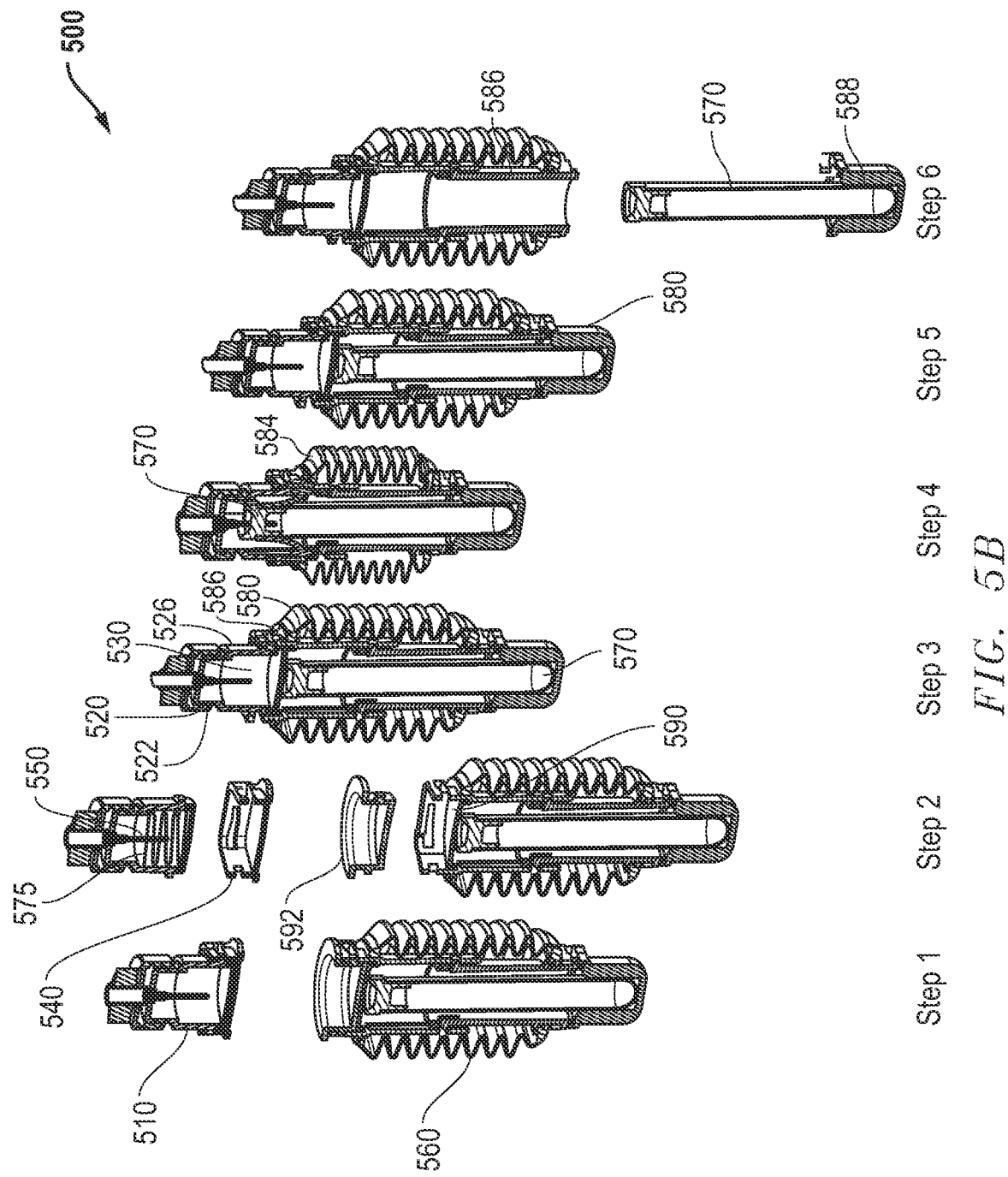

SAMPLING SYSTEM AND METHOD OF USING THE SAME

CROSS-REFERENCE TO RELATED APPLICATION(S)

This application claims priority under 35 U.S.C. § 119(e) to U.S. Provisional Application No. 63/039,848, entitled "SAMPLING SYSTEM AND METHOD OF USING THE SAME," by Clemens E. ZOELLNER et al., filed Jun. 16, 2020, which is assigned to the current assignee hereof and incorporated herein by reference in its entirety.

FIELD OF THE DISCLOSURE

The present disclosure relates to sampling systems, and more particularly to, sampling systems for sampling fluids from vessels in aseptic environments.

RELATED ART

Sampling systems are generally known to sample fluids from vessels into sampling containers. In some applications, sampling systems may sample cells with a sampling container from a cell culture container such as a cell culture container where sterility of the container and the sampling container is desired. Conventionally, sampling may include connecting a syringe to a port of the cell culture container, which requires careful and detailed procedures to make sure sterility is maintained to avoid contamination, adding undesired complexity and time to the sampling process. Further, conventional systems may cause undesired cell settling in the cell culture container or the sampling container. Therefore, improvements in sampling systems are needed, which allow for simple and robust sampling with minimal contamination risk to the container or the sampling container.

BRIEF DESCRIPTION OF THE DRAWINGS

Embodiments are illustrated by way of example and are not limited in the accompanying figures.

FIG. 4A illustrates an exploded view of the sterile sampling container assembly according to a number of embodiments.

FIG. 4B illustrates a cross-sectional view of the sterile sampling container assembly as seen along line C-C in FIG. 4A according to a number of embodiments.

FIG. 5B illustrates a cross-sectional view of a method of using the sampling system as seen along line D-D in FIG. 5A according to a number of embodiments.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single embodiment is described herein, more than one embodiment may be used in place of a single embodiment. Similarly, where more than one embodiment is described herein, a single embodiment may be substituted for that more than one embodiment.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the sampling system arts.

The following disclosure describes sampling systems to achieve adequate and efficient sampling while maintaining aseptic environments (e.g., closed aseptic system). The concepts are better understood in view of the embodiments described below that illustrate and do not limit the scope of the present invention.

Figure 1:
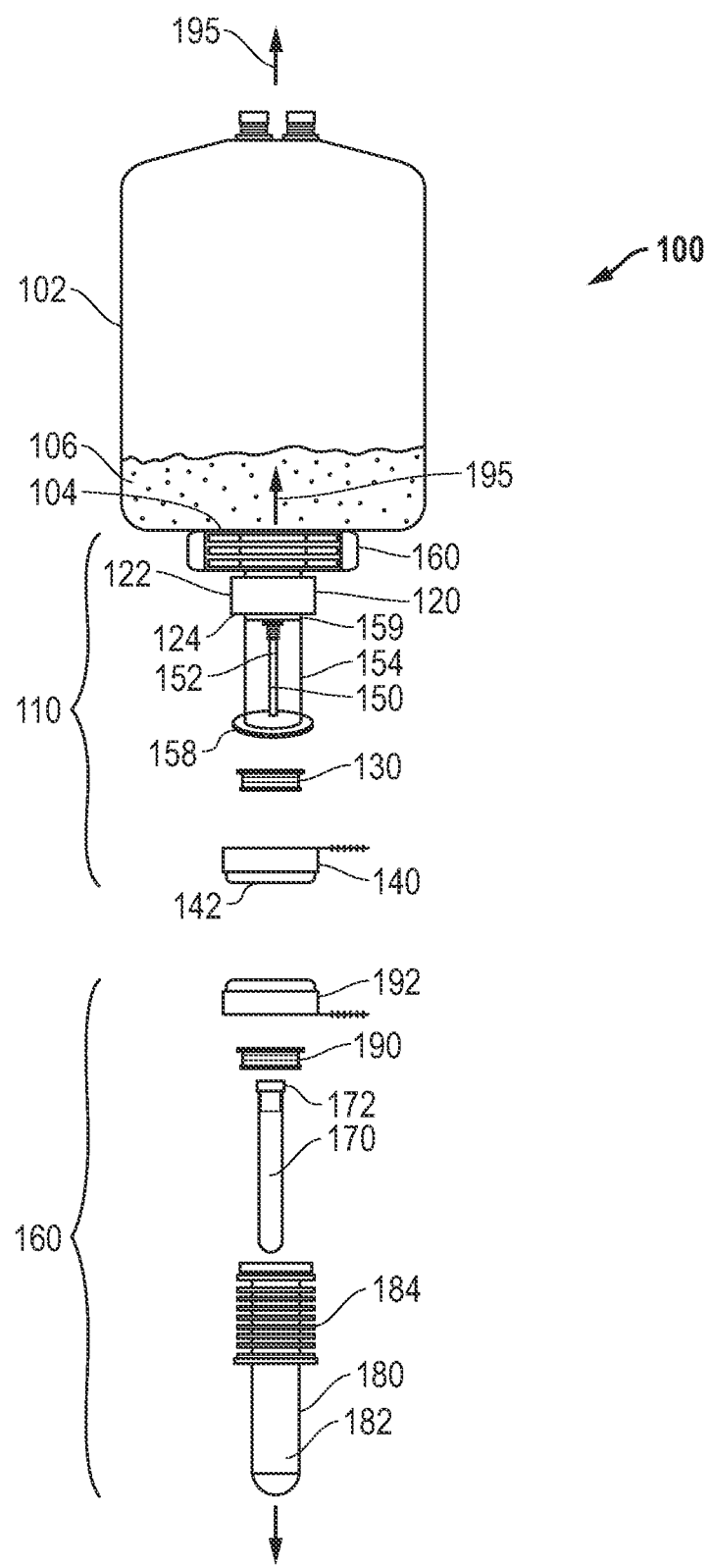
FIG. 1 illustrates an exploded view of a sampling system according to a number of embodiments of the present disclosure.

For purposes of illustration, FIG. 1 shows an exploded view of a sampling system according to a number of embodiments of the present disclosure. The sampling system 100 may be oriented down a central axis 195. As best illustrated in FIG. 1, the sampling system 100 may include a sterile dispenser assembly 110 operably connected to a vessel 102, and a detachable sterile sampling container assembly 160.

As illustrated in FIG. 1, the vessel 102 may house a fluid 106 designated to be sampled from. The vessel 102 may be a cell culture container such as, but not limited to, a cell culture bag. The vessel 102 may be a bioreactor. The fluid 106 may be a biological media. The fluid 106 may be cells or a cell culture mixture.

As illustrated in FIG. 1, the sampling system 100 may include a sterile dispenser assembly 110. The sterile dispenser assembly 110 may be operatively connected to a vessel 102 through a port 104. In a number of embodiments, a plurality of sterile dispenser assemblies 110 may be operatively connected to a vessel 102 through a plurality of ports 104. In a number of embodiments, a plurality of sterile dispenser assembly 110 may be operatively connected to a vessel 102 through a plurality of branches from a single port 104.

The sterile dispenser assembly 110 may include a valve 120. The valve 120 may include a valve body 122 and retention feature 124 which will be described in more detail below. The sterile dispenser assembly 110 may include a needle 150. In some embodiments, the valve 120 may dispense fluid from the vessel 102. In particular embodiments, the valve 120 may be operatively connected to the needle 150 to dispense fluid from the vessel 102. The sterile dispenser assembly 110 may further include a membrane 130. In a number of embodiments, the membrane 130 may be in the form of a breathable valve membrane.

The sterile dispenser assembly 110 may further include a sterile dispenser assembly housing 158 overlying and at least partially surrounding the needle 150. The sterile dispenser assembly housing 158 can cover exposed portions of the sterile dispenser assembly 110 which might come into contact with contaminant during operational usage. The sterile dispenser assembly housing 158 may include a needle cover 154 at least partially surrounding the needle 150. The sterile dispenser assembly housing 158 can be adapted to couple to the valve 120, the needle 150 or both through an interface 159. The interface 159 may include at least one of a barbed interface, a bayonet connection, a threaded engagement interface, a clip or tab interface, another fluid conduit interface, or any combination. The needle 150 may further include a needle sleeve 152 overlying and protecting the needle 150. The sterile dispenser assembly 110 may further include a disposable cap 140 overlying the sterile dispenser assembly 110.

As further illustrated in FIG. 1, the sampling system 100 may further include a detachable sterile sampling container assembly 160. The detachable sterile sampling container assembly 160 may include a sampling container 170. The sampling container 170 may be a tube or other container may house and transport a fluid 106. It may be understood that the sampling container 170 may contain a vacuum to induce fluid entry. The sampling container 170 may include a sampling container cap 172 disposed over the sampling container 170. The detachable sterile sampling container assembly 160 may include a sampling container housing 180. The sampling container housing 180 may at least partially surround, enclose, or encapsulate the sampling container 170. The sampling container housing 180 may further include a compressible portion 184. The compressible portion 184 may include bellows or other similar means to adjust the size of the sampling container housing 180. The detachable sterile sampling container assembly 160 may include a membrane 190. The detachable sterile sampling container assembly 160 may further include a disposable cap 192 overlying the detachable sterile sampling container assembly 160.

Figure 2A:
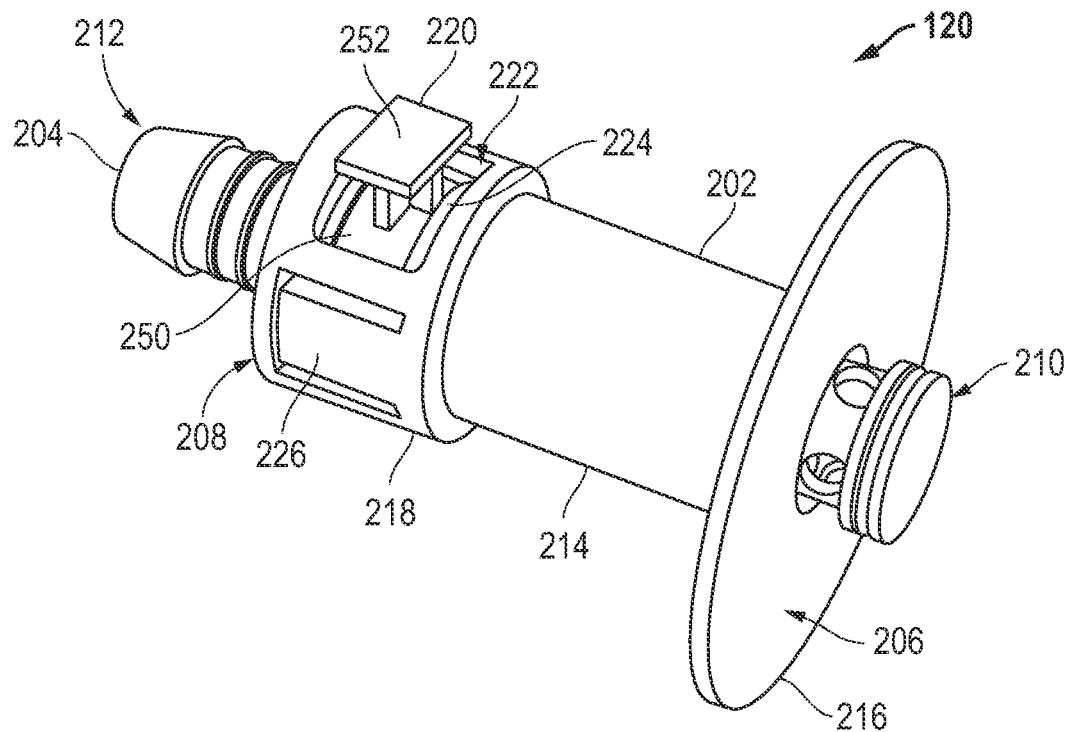
FIG. 2A illustrates a perspective view of a valve of the sterile dispenser assembly in accordance with a number of embodiments of the present disclosure.

For purposes of illustration, FIG. 2A shows a perspective view of the valve of the sterile dispenser assembly according to a number of embodiments of the present disclosure. The valve 120 can generally include a valve body 202 and a valve stem 204 disposed at least partially within the valve body 202. The valve stem 204 can be adapted to translate within an opening in the valve body 202 to move between open and closed configurations. The valve stem 204 may be operatively connected to a needle (not shown) to dispense the fluid as shown in FIG. 1. In the open configuration, the valve 120 can permit fluid passage from the port of the vessel through the valve 120 into the needle. In the closed configuration, the valve 120 can prevent fluid passage from the port of the vessel through the valve 120 into the needle. The valve body 202 can include a cylindrical portion 214 coupled with a flange 216. In an embodiment, the flange 216 can be coupled with the cylindrical portion 214 at, or adjacent to, a first longitudinal end 206 of the valve body 202. In a particular embodiment, the flange 216 can be adapted to be welded to the vessel. In a more particular embodiment, the flange 216 can be adapted to be sonically welded to the vessel.

In certain instances, the cylindrical portion 214 of the valve body 202 can include an operational zone 218 wherein an operator can manipulate the valve 120, such as view the valve stem 204, adjust the valve stem 204, adjust a retention feature 1220 adapted to selectively maintain the valve stem 204 at a desired configuration, or a combination thereof. In an embodiment, the operational zone 218 may be spaced apart from the flange 216. In a more particular embodiment, the operational zone 218 can be disposed at, or adjacent to, the second longitudinal end 208 of the valve body 202.

In an embodiment, the valve 120 can be adjustable between a closed configuration and an open configuration as described in more detail below. In a particular embodiment, the valve 120 can be repeatedly adjustable between the open and closed configurations. In such a manner, an operator can selectively toggle the valve 120 between open and closed configurations. In another particular embodiment, the valve 120 can be adjustable between the open and closed configuration only once. That is, for example, the valve 120 can be adapted for single-use operations. By way of non-limiting example, the valve 120 can translate from the closed configuration to the open configuration and remain fixed in the open configuration. A stay, clip, or alternate one-time mechanism can prevent translation of the valve stem 204 after a single adjustment thereof. This may be particularly suitable for applications with single-use systems, such as with single-use vessels such as biopharmaceutical mixing bags. In certain instances, the valve 120 can include a single-use feature (not illustrated) adapted to retain the valve stem 204 in the open configuration after movement thereto.

The operational zone 218 of the valve body 202 can include one or more apertures 222 through which the valve stem 204 can be visible from an external environment. In an embodiment, the one or more apertures 222 can include a retention feature aperture 224 adapted to permit user engagement with the retention feature 220. In another embodiment, the one or more apertures 222 can include a clip feature 226 adapted to prevent undesired disengagement of the valve stem 204 from the valve body 202. The clip feature 226 can include, for instance, a portion of the valve body 202 having a lip or other retention feature adapted to prevent removal of the valve stem 204 from the valve body 202. During installation of the valve stem 204 with the valve body 202, the clip feature 226 can displace in a radial direction (e.g., radially outward) to permit passage of the valve stem 204 therethrough. After installation, the clip feature 226 can rebound toward the valve stem 204 and prevent undesired removal of the valve stem 204 from the valve body 202. In a particular instance, the valve 120 can include one clip feature 226. In other instances, the valve 120 can include a plurality of clip features 226, such as at least two clip features 226. The plurality of clip features 226 can be spaced apart from one another, such as in different apertures 222 within the operational zone 218 or within a same aperture 222.

Figure 2B:
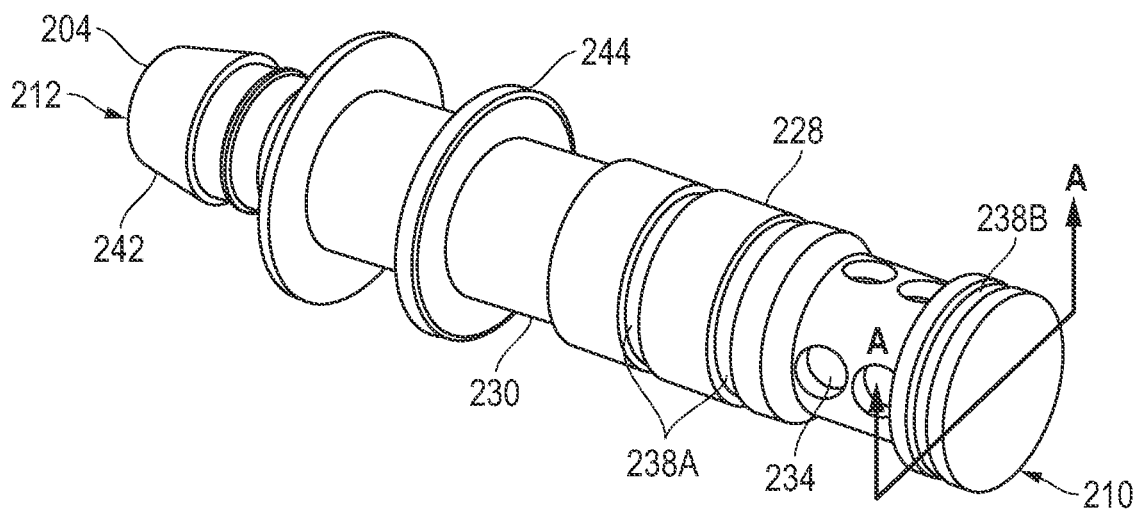
FIG. 2B illustrates a perspective view of a valve stem of the valve in accordance with a number of embodiments of the present disclosure.
Figure 2C:
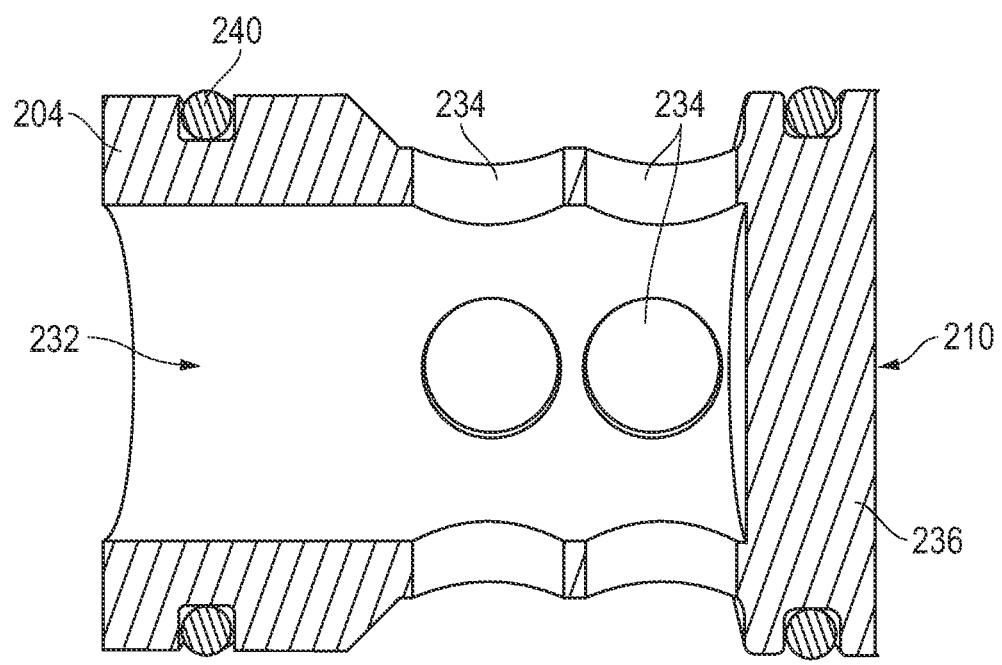
FIG. 2C illustrate a cross-sectional view of the valve stem as seen along line A-A in FIG. 2B in accordance with a number of embodiments of the present disclosure.

For purposes of illustration, FIG. 2B shows a perspective view of a valve stem of the valve in accordance with a number of embodiments of the present disclosure. For purposes of illustration, FIG. 2C shows a cross-sectional view of the valve stem as seen along line A-A in FIG. 2B in accordance with a number of embodiments of the present disclosure. Referring initially to FIG. 2B, in an embodiment, the first longitudinal end 206 of the valve body 202 and the first longitudinal end 210 of the valve stem 204 can be disposed along a generally same plane when the valve 120 is in the closed configuration. In a more particular embodiment, the first longitudinal ends 206 and 210 can be disposed along a same plane when the valve 120 is in the closed configuration. The second longitudinal end 208 of the valve body 202 can be disposed between the first and second longitudinal ends 210 and 212 of the valve stem 204 when the valve 120 is in the closed configuration.

As shown in FIG. 2B, the valve stem 204 can generally include a body 228 having a sidewall 230, such as a generally cylindrical sidewall. The sidewall 230 can define a central lumen 232 (as shown in FIG. 2C) and at least one opening 234 extending through the sidewall 230. In an embodiment, the at least one opening 234 can extend from the external environment to the central lumen 232. That is, the central lumen 232 can be in fluid communication with the external environment through the at least one opening 234. The at least one opening 234 can include a plurality of openings. In an embodiment, the valve stem 204 can have a closed longitudinal end. In a more particular embodiment, the first longitudinal end 210 of the valve stem 204 can be closed. In such a manner, fluid can neither enter nor exit the central lumen 234 of the valve stem 204 through the longitudinal end 210 thereof. In an embodiment, the first longitudinal end 210 of the valve stem 204 includes a cap 236. The cap 236 can have a generally planar surface. The cap 236 can close the lumen 232 at the first longitudinal end 210. In an embodiment, the cap 236 can be integral with the sidewall 230 of the valve stem 204. For instance, the cap 236 can be monolithic with the sidewall 230. In another embodiment, the cap 236 can include a discrete element coupled with the sidewall 230.

Still referring to FIG. 2B, in an embodiment, the valve stem 204 can define a plurality of grooves 238 each adapted to receive one or more seals 240 (shown best in FIG. 2C). In an embodiment, the grooves 238 can be adapted to receive O-rings extending around a circumference of the valve stem 204. In a more particular embodiment, the seals 240 can sit within the grooves 238 and extend past an outer surface of the valve stem 204 such that they can sealingly engage with an inner surface of the valve body 202. The seals 240 can prevent fluid flow between the valve stem 204 and the valve body 202 when the valve 120 is in both open and closed configurations.

In an embodiment, the valve stem 204 can include an interface 242 adapted to receive and engage with the needle. In an embodiment, the interface 242 can be disposed at or adjacent to the second longitudinal end 212 of the valve stem 204. In an embodiment, the interface 242 can be adapted to form an interference fit with the needle. In a more particular embodiment, the interface 242 can include a barbed interface adapted to receive and engage the needle. In another embodiment, the interface 242 can include a bayonet connection, a threaded engagement interface, a clip or tab interface, another fluid conduit interface, or any combination thereof adapted to receive and engage the needle with a similar coupling interface on or attached to the needle.

In an embodiment, the valve stem 204 can define a locking flange 244 extending from the sidewall 230. The locking flange 244 can be adapted to engage with the retention feature 220, the valve stem 204, or both in order to selectively maintain the valve 120 in the open and closed configurations. In an embodiment, the locking flange 244 can be visible from an external location to the valve body 202 when the valve stem 204 is installed therewith. In a more particular embodiment, the locking flange 244 can be at least partially visible through the aperture 222 of the valve body 204. In certain instances, the locking flange 244 can be visible from the external location when the valve 120 is in the open and closed configurations.

In an embodiment, the clip feature 226 can be adapted to engage with a complementary locking flange 256 of the valve stem 204 to prevent the valve stem 204 from disengaging with the valve body 202. In certain instances, the clip feature 226 can be at least partially disposed between the locking flange 244 and the complementary locking flange 256. More particularly, in an embodiment, a lip (not illustrated) of the clip feature 226 can be disposed between the locking flange 244 and the complementary locking flange 256. In certain instances, the locking flange 244 and complementary locking flange 256 can prevent axial displacement of the valve stem 204 from the valve body 202 in both longitudinal directions.

Figure 2D:
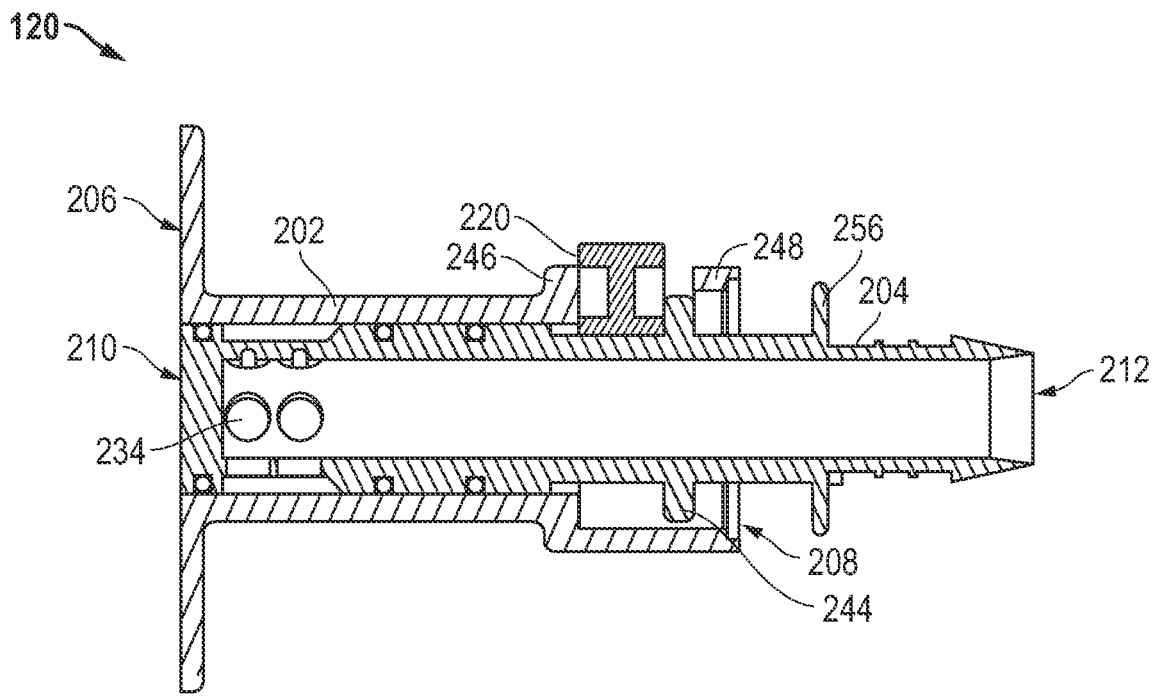
FIG. 2D illustrates the valve in the closed configuration in accordance with a number of embodiments of the present disclosure.

FIG. 2D shows the valve in the closed configuration in accordance with a number of embodiments of the present disclosure. As shown in FIG. 2D, the valve body 202 can define a first stop feature 246 and a second stop feature 248 spaced apart from one another. In an embodiment, the first and second stop features 246 and 248 can be spaced apart from one another by an adjustment length, $L_A$. The locking flange 244 can be translatable along the adjustment length, $L_A$.

In an embodiment, the locking flange 244 can be adapted to contact the first stop feature 246 when the valve 120 is in the open configuration and contact the second stop feature 248 when the valve 120 is in the closed configuration. The retention feature 220 can be installed between the first and second stop features 246 and 246 to retard movement of the retention feature 220 when the valve 120 is selectively in the open or closed configurations. In an embodiment, the retention feature 220 can be adapted to contact the first stop feature 246 when the valve 120 is in the closed configuration and contact the second stop feature 248 when the valve 120 is in the open configuration.

Figure 2E:
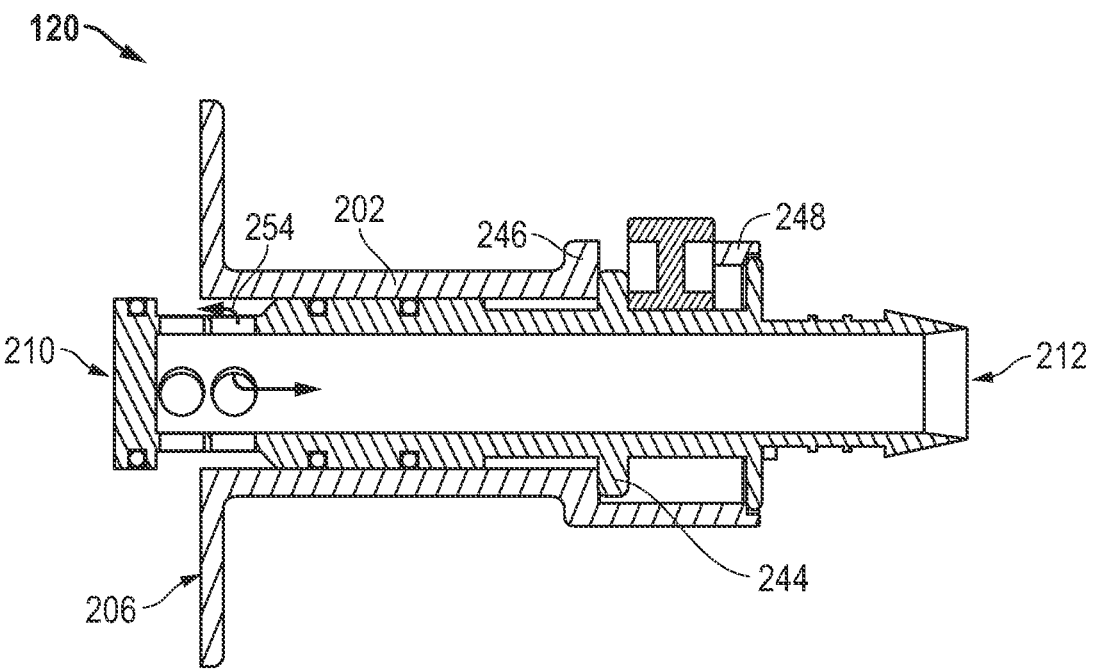
FIG. 2E illustrates the valve in the open configuration in accordance with a number of embodiments of the present disclosure.

FIG. 2E shows the valve in the open configuration in accordance with a number of embodiments of the present disclosure. As shown in FIG. 2E, the valve 120 in the open configuration may include the one or more openings 234 extending at least partially beyond the first longitudinal end 206 of the valve body 202. The retention feature 220 may be disposed between the locking flange 244 and the second stop feature 248. In this position, fluid can pass from the second longitudinal end 212 of the valve stem 204, through the central lumen 232, and through the one or more openings 234 into the needle. Alternatively, fluid can pass through the one or more openings 234, through the central lumen 232, and out of the second longitudinal end 212 of the valve stem 204.

The retention feature 220 can generally define a body adapted to be installed within the aperture 222 of the valve body 202. Referring again to FIG. 2A, the retention feature 220 can include a clip portion 250 adapted to seat at least partially around the valve stem 204 and a grippable portion 252 extending from the clip portion 250 to permit user grip therewith. The retention feature 220 can be moved, such as selectively moved, between an engaged position with the valve 120 and a disengaged position with respect to the valve 120. In an embodiment, the retention feature 220 can be detachable from the valve body 202 or valve stem 204. For instance, the retention feature 220 can be spaced apart from the valve stem 204 and valve body 202 when in the disengaged position.

Figure 2G:
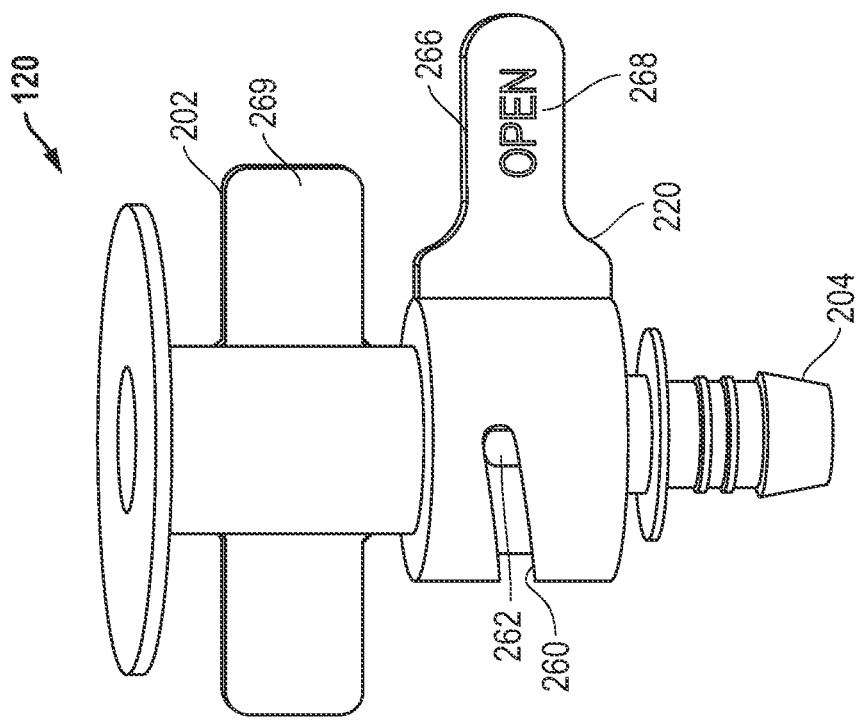
FIG. 2G illustrates a perspective view of a valve of the sterile dispenser assembly in accordance with a number of embodiments of the present disclosure.
Figure 2H:
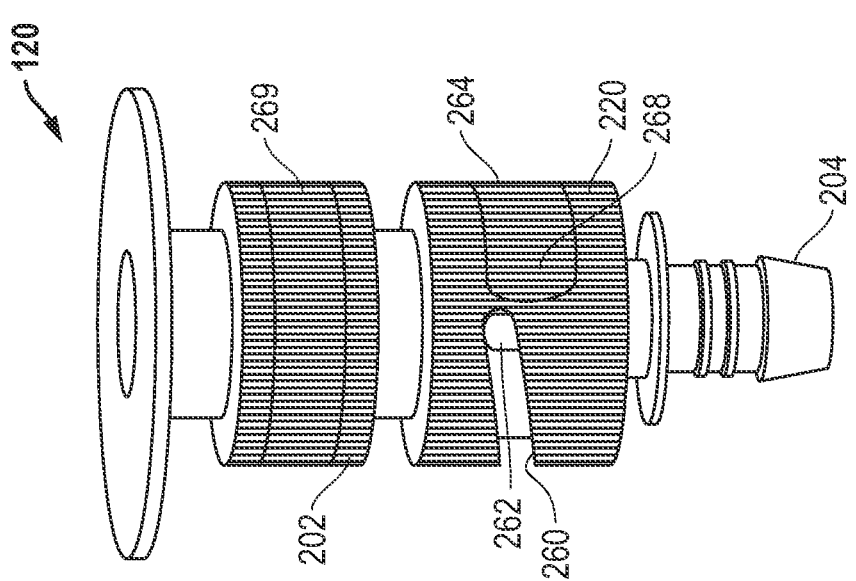
FIG. 2F illustrates a perspective view of a valve of the sterile dispenser assembly in accordance with a number of embodiments of the present disclosure.

FIGS. 2F and 2G, which illustrate perspective views of valves in accordance with a number of embodiments of the present disclosure. As shown in FIGS. 2F and 2G, in another embodiment, the retention feature can be adapted to remain in contact with at least one of the valve stem 204 and valve body 202 when in the disengaged position. In a number of embodiments, a retention feature 220 can be rotatably coupled with the valve body 202 or valve stem 204. The valve stem 204 can translate relative to the valve body 202 upon rotatably biasing the retention feature 220. Thus, for instance, the valve 120 can move between open and closed configurations upon rotational movement of the retention feature 220.

As illustrated, the retention feature 220 can include a ramp 260. The ramp 260 can extend around at least a portion of the circumference of the retention feature 220, such as at least 10% of the circumference, at least 20% of the circumference, at least 30% of the circumference, at least 40% of the circumference, or at least 50% of the circumference. The ramp 260 can define a ramp angle, as measured with respect to a plane perpendicular to an axis of the valve stem 104, of at least 1°, at least 2°, at least 3°, at least 4°, at least 5°, at least 10°, at least 15°, at least 20°, at least 25°, or at least 30°. In an embodiment, the ramp 260 can include a cutout in the retention feature 220. In a particular embodiment, the cutout can extend through a radial thickness of the retention feature 220, such as through an entire radial thickness of the retention feature 220.

In an embodiment, a portion 262 of the valve stem 204 can extend through the valve body 202 to the retention feature 2002. The portion 262 can engage with the ramp 260 such that rotationally biasing the retention feature 220 affects linear translation of the valve stem 204 relative to the valve body 202. In turn, the valve 120 can move between the open and closed configurations upon rotational movement imparted to the retention feature 220. In an embodiment, the ramp 260, portion 262, or both can include tactile indications to the operator when the retention feature 220 is transitioned an acceptable rotational distance. Further, the ramp 260, portion 262, or both can be adapted to maintain the retention feature 220 in the desired configuration after completion of the rotational adjustment thereto.

In certain instances, the retention feature 220 can include a grippable portion, such as a textured surface 264 (FIG. 2F), a tab or projection 266 (FIG. 2G), another grippable surface, or any combination thereof. The retention feature 220 can include indicia 268 to indicate directional operation of the retention feature 220. For instance, the indicia 268 can indicate which direction the retention feature 220 is adjusted to open and close the valve 120. The indicia can include a color, a text or symbol, a surface characteristic, or another indicating element adapted to indicate to the operator how to adjust the valve 120. One or more complementary grippable elements 269 can be included along the valve body 202 to facilitate easier rotational biasing of the retention feature 220 relative to the valve body 202.

Other examples of the retention feature (not shown) may be translatably coupled with the valve body 202 or valve stem 204. This retention feature can include an adjustment zone and a lock zone. The adjustment zone can correspond with an area of the retention feature adapted to permit adjustment of the valve stem between open and closed configurations. The lock zone can correspond with an area of the retention feature adapted to prevent adjustment of the valve stem between open and closed configurations. Engageable portions, including tabs, projections, textured surfaces, other grippable elements, or combinations thereof, can be disposed on the retention feature to permit operator access and adjustment thereof. In this embodiment, the valve body 202 can include a cutout adapted to receive the retention feature. In a particular embodiment, the cutout can be shaped to receive the engageable portions of the retention feature.

In certain instances, an opening force, $F_O$, required to translate the valve stem 204 to the open configuration is approximately equal to a closing force, $F_C$, required to move the valve stem 204 to the closed configuration. In a more particular embodiment, $F_O$ and $F_C$ can be approximately equal when fluid pressures on both longitudinal ends of the valve stem 204 are approximately equal. That is, in an embodiment, the valve 120 can be unbiased by a spring. More particularly, in an embodiment, the valve 120 can be essentially free of a spring or biasing means adapted to bias the valve stem 204, valve body 202, or both. Accordingly, moving the valve stem 204 can be performed with a generally same force in the opening and closing directions.

In a number of embodiments, the valve may lessen the effect of cell settling within the vessel, valve, or sampling system. In a number of embodiments, the valve may connect with the port and may have an internal shut-off at the port connection that blocks cells from entering the valve until the valve is in an open configuration through the lock zone. In other words, cells within the vessel will not settle in the valve or port and provide an unrepresentative sample of the cells in the vessel due to the use of the valve according to embodiments described herein.

In other embodiments, the port of the vessel may connect to the sterile dispenser assembly 310 in other ways that don't include a valve. For example, the valve 320 may be replaced by a septum as described in more detail below.

Figures 3A, 3B:
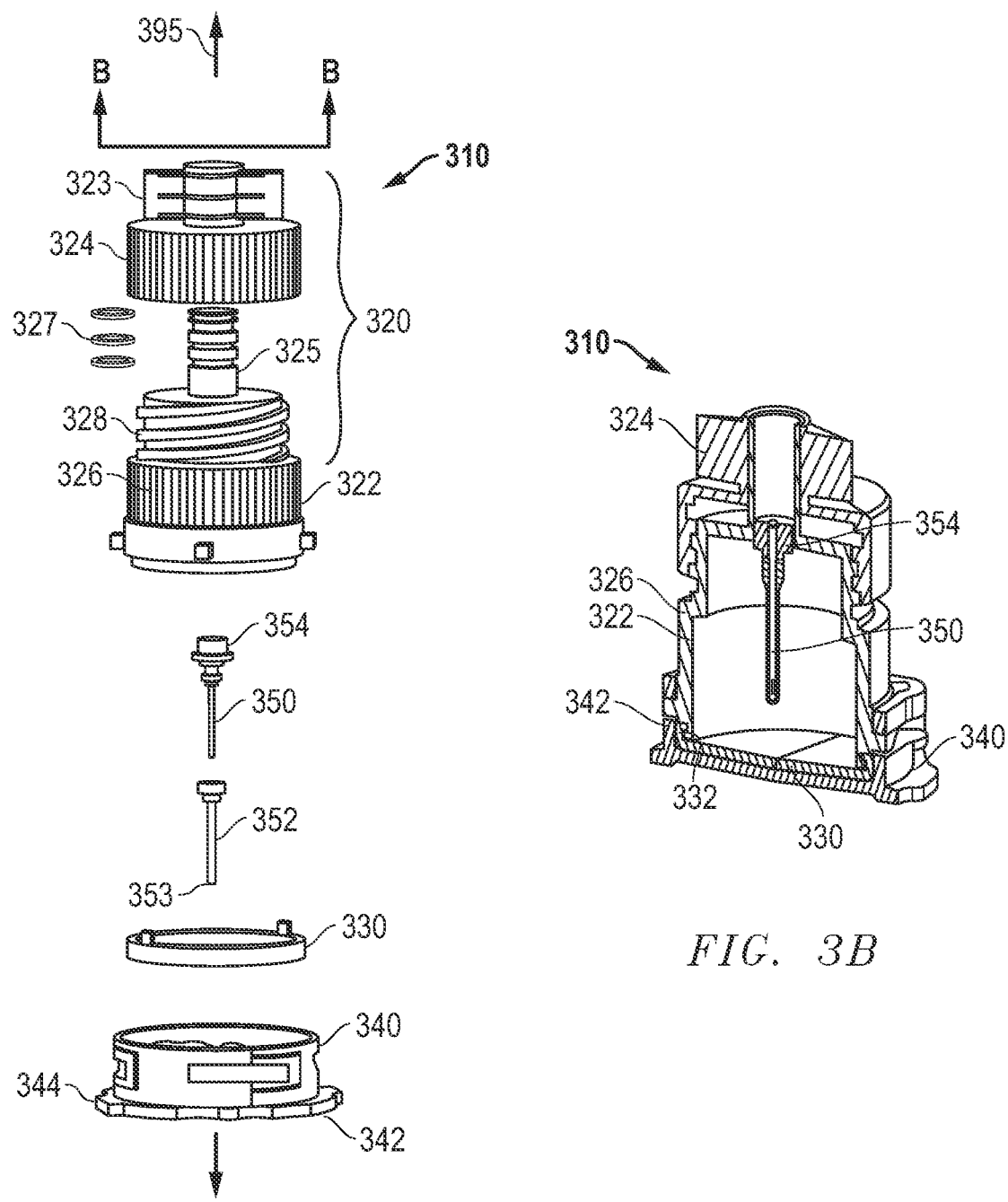
FIG. 3A illustrates an exploded view of the sterile dispenser assembly according to a number of embodiments.
FIG. 3B illustrates a cross-sectional view of the sterile dispenser assembly as seen along line B-B in FIG. 3A according to a number of embodiments.

FIG. 3A shows an exploded view of the sterile dispenser assembly according to a number of embodiments. FIG. 3B shows a cross-sectional view of the sterile dispenser assembly as seen along line B-B in FIG. 3A according to a number of embodiments. As stated above and as shown in FIG. 3A, the sterile dispenser assembly 310 may be down a central axis 395, and may include a valve 320, a needle 350, and a membrane 330. The valve 320 shown with a valve body 322 comprising a first piece 324 and a second piece 326. The first piece 324 may coincide at least partially with the cylindrical portion described above and may include a retention feature 323 as described above. The second piece 326 may coincide with the valve stem described above. The second piece 326 may operatively couple to the first piece 324 through an interface 328 including at least one of a barbed interface, a bayonet connection, a threaded engagement interface, a clip or tab interface, another fluid conduit interface, or any combination. Further, the second piece 326 may include a plurality of grooves 325 each adapted to receive one or more seals or O-rings 327 as described above. The second piece 326 of the valve 320 may couple to the needle 350 as described above. The second piece 326 may operatively couple to the needle 350 through an interface 354 on the needle 350 including at least one of a barbed interface, a bayonet connection, a threaded engagement interface, a clip or tab interface, another fluid conduit interface, or any combination. FIG. 3B shows this interface 354 in more detail. Further, the needle 350 may include a needle sleeve 352 to protect the needle 350 from damage and the environment. In some embodiments, the needle sleeve 352 may completely enclose the needle 350. The needle sleeve 352 may be removable. In other embodiments, the needle sleeve 352 may have a bore 353 through which the needle 350 may extend through the needle sleeve 352. The needle 350 itself may have a tapered hole to wipe during use, eliminating unnecessary fluid dispersion.

Further, as stated above, sterile dispenser assembly 310 may include a housing. However, in the embodiment shown in FIG. 3B, the housing may be encompassed by the second piece 326 of the valve 320. Further, as stated above, sterile dispenser assembly 310 may include a disposable cap 340. The disposable cap 340 can cover exposed portions of the sterile dispenser assembly 310 which might come into contact with contaminant during operational usage. The disposable cap 340 can be adapted to secure with the housing (as shown in FIG. 1), or the second piece 326 of the valve 320 (as shown in FIG. 3B). The disposable cap 340 may operatively couple to the housing or the second piece 326 of the valve 320 through an interface 342 including at least one of a barbed interface, a bayonet connection, a threaded engagement interface, a clip or tab interface, another fluid conduit interface, or any combination. In certain instances, the disposable cap 340 can include a grippable element 344 adapted to facilitate easier gripping and removal of the disposable cap 340. The grippable element 344 can extend from the side of the disposable cap 340 and project therefrom to permit user grip therewith. In certain instances, the disposable cap 340 can include a single-use cover. In other instances, the disposable cap 340 can be reused. In such embodiments, the grippable element 344 can facilitate easier installation of the disposable cap 340 relative to the sterile dispenser assembly 310.

Further, as stated above, the sterile dispenser assembly 310 may further include a membrane 330. In a number of embodiments, the membrane 330 may be in the form of a breathable valve membrane. The breathable valve membrane may be pentratable by the needle 350 or a component of the sterile sampling container assembly as described in further detail below. As shown best in FIG. 3B, the membrane 330 may operatively couple to the housing or the second piece 326 of the valve 320 through an interface 332 including at least one of a barbed interface, a bayonet connection, a threaded engagement interface, a clip or tab interface, another fluid conduit interface, or any combination thereof, adapted to receive and engage second piece 326 of the valve 320 with a similar coupling interface on or attached to the second piece 326 of the valve 320. The membrane 330 may be made of an elastomeric material. The membrane 330 may be made of a silicone.

In a number of alternative embodiments, the membrane 130 may be a sterile connector. The sterile connector may include a first piece, a second piece, and a cover or tape located on a side of each of the first and second piece. The first piece and the second piece may be coupled and the covers removed to create a sterile connection for fluid flow.

FIG. 4A shows an exploded view of the sterile sampling container assembly according to a number of embodiments. FIG. 4B shows a cross-sectional view of the sterile sampling container assembly as seen along line C-C in FIG. 4A according to a number of embodiments. Referring to FIGS. 4A-4B and as stated above, the detachable sterile sampling container assembly 460 may be down a central axis 495 and may include a sampling container 470, a sampling container cap 472 disposed over the sampling container 470, a sampling container housing 480, a membrane 490, and a disposable cap 492. In a number of embodiments, the sampling container housing 480 may include a top portion 486, a bottom portion 488 and a compressible portion 484 disposed between the top portion 486 and the bottom portion 488. In a number of embodiments, the top portion 486 and a bottom portion 488 may be made of a rigid material. The compressible portion 484 may allow the top portion 486 to move relative to the bottom portion 488 or allow the bottom portion 488 to move relative to the top portion 486. In a number of embodiments, as shown in FIGS. 4A-4B, the compressible portion 484 include bellows 485 or other similar means to adjust the position of the sampling container of the sampling container housing 480. In certain embodiments, the compressible portion 484 may include a flexible or elastic material such as an elastomer. In some embodiments, the compressible portion 484 may include a rolling portion disposed between the two pieces of the sampling container housing 480. In a number of embodiments, the rolling portion may be an O-ring. In some embodiments, the compressible portion 484 may include a rolling portion disposed between the two pieces of the sampling container housing 480 as shown in more detail below.

In a number of embodiments, the compressible portion 484 may have a deflated configuration and an expanded configuration. In an expanded configuration, the compressible portion 484 may allow maximum distance between the top portion 486 and the bottom portion 488 along the central axis 495. In a deflated configuration, the compressible portion 484 may minimize or lessen the distance between the top portion 486 and the bottom portion 488 along the central axis 495. In the deflated configuration, the compressible portion 484 may push the sampling container 470 through the membrane 490 of the sterile sampling container assembly 480 and into proximity with the needle, allowing the needle to dispense fluid into the sampling container 470 while maintaining a closed aseptic system as described in more detail below.

In certain embodiments, the bottom portion 488 may be further divided into a first bottom portion 488*a* and a second bottom portion 488*b*. In an embodiment, the first bottom portion 488*a* can include an interface 489 adapted to receive and engage with the second bottom portion 488*b*. In an embodiment, the interface 489 can be adapted to form an interference fit with the second bottom portion 488*b*. In a more particular embodiment, the interface 489 can include a barbed interface adapted to receive and engage the second bottom portion 488*b*. In another embodiment, the interface 489 can include a bayonet connection, a threaded engagement interface, a clip or tab interface, another fluid conduit interface, or any combination thereof adapted to receive and engage the second bottom portion 488*b* with a similar coupling interface on or attached to the second bottom portion 488*b*. In a number of embodiments, the bottom portion 588*b* may be spring-loaded.

Further, sterile sampling container assembly 460 may include a membrane 490. In a number of embodiments, the membrane 490 may be in the form of a breathable valve membrane. The breathable valve membrane may be penetrate-able by the needle or a component of the sterile sampling container assembly as described in further detail below. As shown best in FIG. 4B, the membrane 490 may operatively couple to the top portion 486 of the sampling container housing 480 through an interface 492 including at least one of a barbed interface, a bayonet connection, a threaded engagement interface, a clip or tab interface, another fluid conduit interface, or any combination thereof, adapted to receive and engage the top portion 486 of the sampling container housing 480 with a similar coupling interface on or attached to the top portion 486 of the sampling container housing 480. The membrane 490 may be made of an elastomeric material. The membrane 490 may be made of a silicone.

In a number of alternative embodiments, the membrane 490 may be a sterile connector. The sterile connector may include a first piece, a second piece, and a cover located on a side of each of the first and second piece. The first piece and the second piece may be coupled and the covers removed to create a sterile connection for fluid flow.

As stated above, the sterile sampling container assembly 460 may include a disposable cap 492. The disposable cap 492 can cover exposed portions of the sterile sampling container assembly 460 which might come into contact with contaminant during operational usage. The disposable cap 440 can be adapted to secure with top portion 486 of the sampling container housing 480 (as shown in FIG. 4B). The disposable cap 492 may operatively couple to the top portion 486 of the sampling container housing 480 through an interface 494 including at least one of a barbed interface, a bayonet connection, a threaded engagement interface, a clip or tab interface, another fluid conduit interface, or any combination thereof, adapted to receive and engage the top portion 486 of the sampling container housing 480 with a similar coupling interface on or attached to the top portion 486 of the sampling container housing 480. In certain instances, the disposable cap 492 can include a grippable element 496 adapted to facilitate easier gripping and removal of the disposable cap 492. The grippable element 496 can extend from the side of the disposable cap 492 and project therefrom to permit user grip therewith. In certain instances, the disposable cap 492 can include a single-use cover. In other instances, the disposable cap 492 can be reused. In such embodiments, the grippable element 496 can facilitate easier installation of the disposable cap 440 relative to the sterile sampling container assembly 460.

Figure 5A:
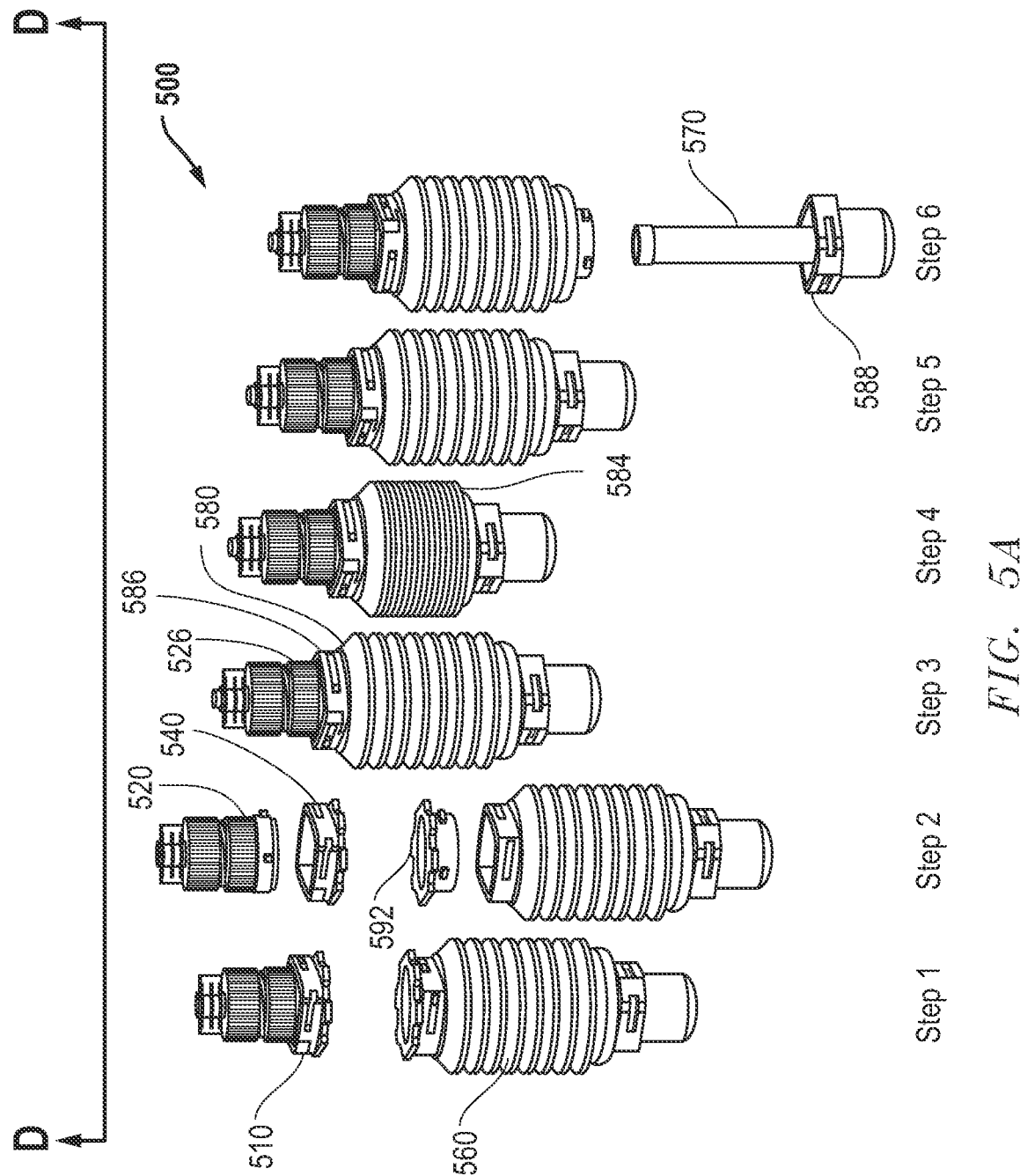
FIG. 5A illustrates an exploded view of a method of using the sampling system according to a number of embodiments.

FIG. 5A shows an exploded view of a method of using the sampling system according to a number of embodiments. FIG. 5B shows a cross-sectional view of a method of using the sampling system as seen along line D-D in FIG. 5A according to a number of embodiments. As shown in FIGS. 5A-5B, the sampling system 500 may include a sterile dispenser assembly 510 and any of the components of the sterile dispenser assembly 510 described herein. Further, the sampling system 500 may include a detachable sterile sampling container assembly 560 and any of the components of the detachable sterile sampling container assembly 560 described herein. Under Step 1 of FIGS. 5A-5B, sterile dispenser assembly 510 and the detachable sterile sampling container assembly 560 are brought into proximity of each other. The sterile dispenser assembly 510 is operatively connected to a vessel containing a fluid (not shown). Under Step 2 of FIGS. 5A-5B, the disposable cap 540 of sterile dispenser assembly 510 and the disposable cap 592 of the detachable sterile sampling container assembly 560 are each removed. Under Step 3 of FIGS. 5A-5B, the second piece 526 of the valve body 522 of the valve 520 of the sterile dispenser assembly 510 and the top portion 586 of the sampling container housing 580 detachable sterile sampling container assembly 560 are brought into contact and coupled at an interface 577. Further, the membranes 530, 590 of the sterile dispenser assembly 510 and the detachable sterile sampling container assembly 560 respectively are brought into proximity of each other. In this way the sterile dispenser assembly 510 and the detachable sterile sampling container assembly 560 are operatively connected. Under Step 4 of FIGS. 5A-5B, the compressible portion 584 of the detachable sterile sampling container assembly 560 is moved to a deflated configuration. This may be done by a user or other mechanical means. The compression pushes the sampling container 570 through the membranes 530, 590 of the sterile dispenser assembly 510 and the detachable sterile sampling container assembly 560 respectively and into proximity with the needle 550, allowing the needle 550 to dispense fluid into the sampling container 570. In some embodiments, the needle 550 may penetrate the sampling container cap 572 of the sampling container 570 to dispense the fluid. Under Step 5 of FIGS. 5A-5B, the compressible portion 584 of the detachable sterile sampling container assembly 560 is moved to an expanded configuration. This may be done by a user or other mechanical means. The compression pushes the sampling container 570 back through the membranes 530, 590 of the sterile dispenser assembly 510 and the detachable sterile sampling container assembly 560 respectively and thereby closing off the sterile dispenser assembly 510 and the detachable sterile sampling container assembly 560. The moving of the compressible portion 584 of the detachable sterile sampling container assembly 560 to an expanded configuration may be aided by a spring 575 located within at least one of the sterile dispenser assembly 510 or the detachable sterile sampling container assembly 560. Lastly, under Step 6 of FIGS. 5A-5B, at least one of the top portion 586 or the bottom portion 588 of the sampling container housing 580 detaches from the rest of the sampling container assembly 560, allowing a user to obtain the sampling container 570, now containing fluid. Throughout this process, a closed aseptic system is maintained. A "closed aseptic system" may be defined herein as a closed sampling system 500 under which fluid can flow and which sterility can be maintained. In some embodiments, the method may only be used once such that a closed aseptic system is maintained in the sterile dispenser assembly 510. In other embodiments, the method may only be used multiple times from a single sterile dispenser assembly 510 while maintaining a closed aseptic system.

Figure 6:
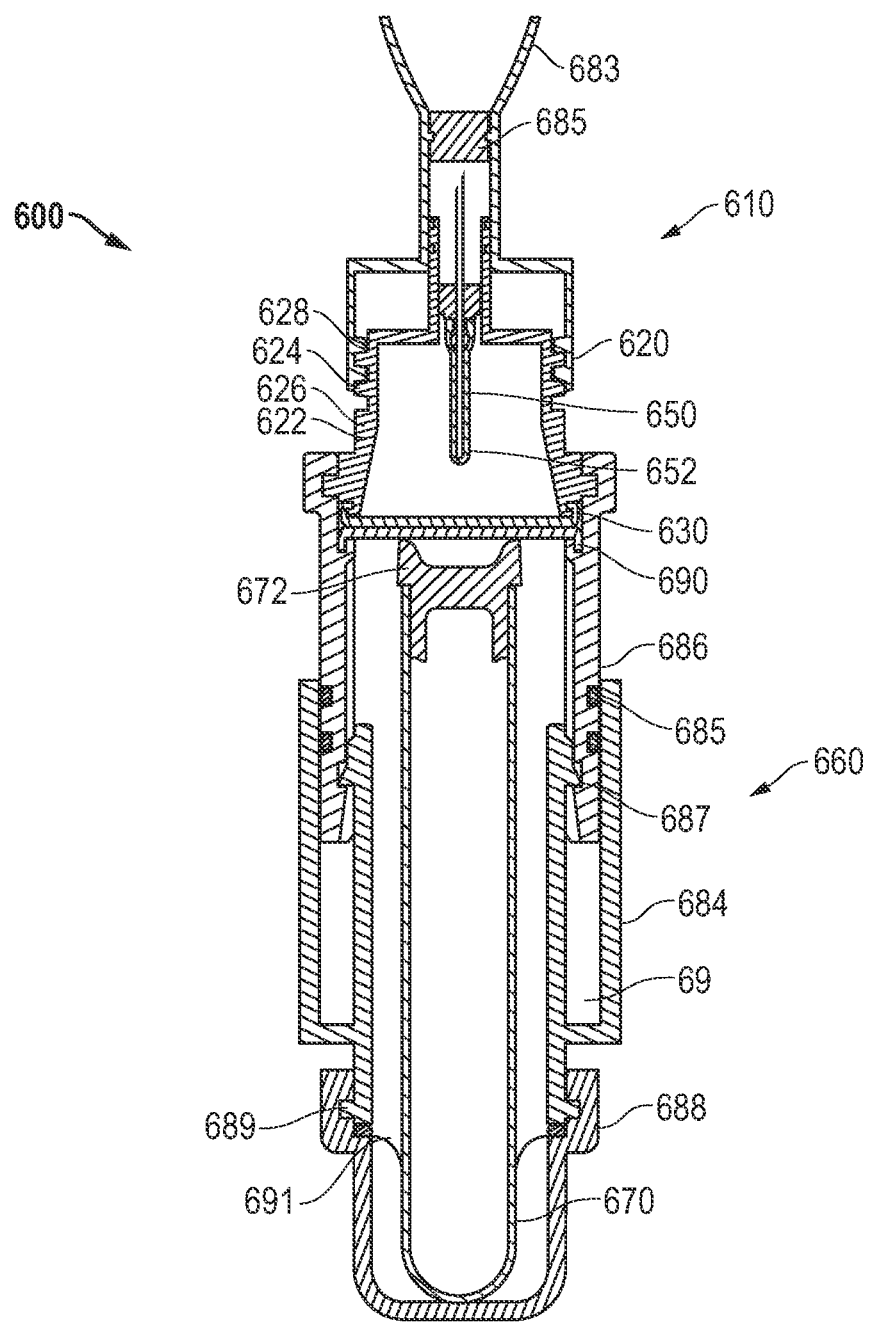
FIG. 6 illustrates a cross-sectional view of a sampling system according to a number of embodiments of the present disclosure.

FIG. 6 illustrates a cross-sectional view of a sampling system according to a number of embodiments of the present disclosure. In an alternative embodiment of the sampling system 600, the sterile dispenser assembly 610 may include a valve 620 shown with a valve body 622 comprising a first piece 624 and a second piece 626 meeting at an interface 628 as described similarly above. The valve 620 may be at least partially surrounding a needle 650 protected by a needle sleeve 652. As shown, the needle may be double-ended. Further, the sterile dispenser assembly 610 may include a membrane 630 as described above. In this alternative embodiment, the valve 620 may connect to the vessel (not shown) through a septum 685 and further include a needle shield 683 to prevent the needle 650 from damage once it enters the vessel. The sterile dispenser assembly 610 may further include a cap (not shown).

In an alternative embodiment of the sampling system 600, the detachable sterile sampling container assembly 660 may include a sampling container 670 with a sampling container cap 672. The detachable sterile sampling container assembly 660 may further include a membrane 690 as described above. In this alternative embodiment, the sampling container housing 680 may include a top portion 686, a compressible portion 684 and a bottom portion 688. In this alternative embodiment, the compressible portion 684 may include interfaces 687, 689 with the top portion 686 and bottom portion 688 respectively. Further, the compressible portion 684 may include a rolling portion 685. In a number of embodiments, the rolling portion may be an O-ring. Further, the bottom portion 688 may be coupled to the sampling container 670 by a spring 691. The detachable sterile sampling container assembly 660 may further include a cap (not shown).

In operation, an upward force on the sampling system 600 forces the needle 650 through the septum 685 where it enters the vessel to draw fluid. The interface 628 between the first piece 624 and the second piece 626 of the valve 620 may be disrupted by this upward force, allowing the needle to move upward to penetrate the septum 685. Further, the compressible portion 684 of the sampling container housing 680 may uncouple with the top portion 686 from the interface 687 and introduce the sampling container 670 to the bottom end of the needle 650 through the dual membranes 630, 690 as described above. As shown in this embodiment, the rolling portions 685 may allow the compressible portion 684 to slide outside the top portion 686 in use and the top portion may fill a cavity 693 in the compressible portion 684 while the sampling container 670 is moving into contact with the needle 650 through an interface between the sterile dispenser assembly 610 and the sterile sampling container assembly 660 similar to step 3 of FIGS. 5A-5B above. All other components of the sampling system may function similarly to how they function in the embodiments described above. In this way, fluid may be sampled from the vessel in a closed aseptic system.

Figure 7A:
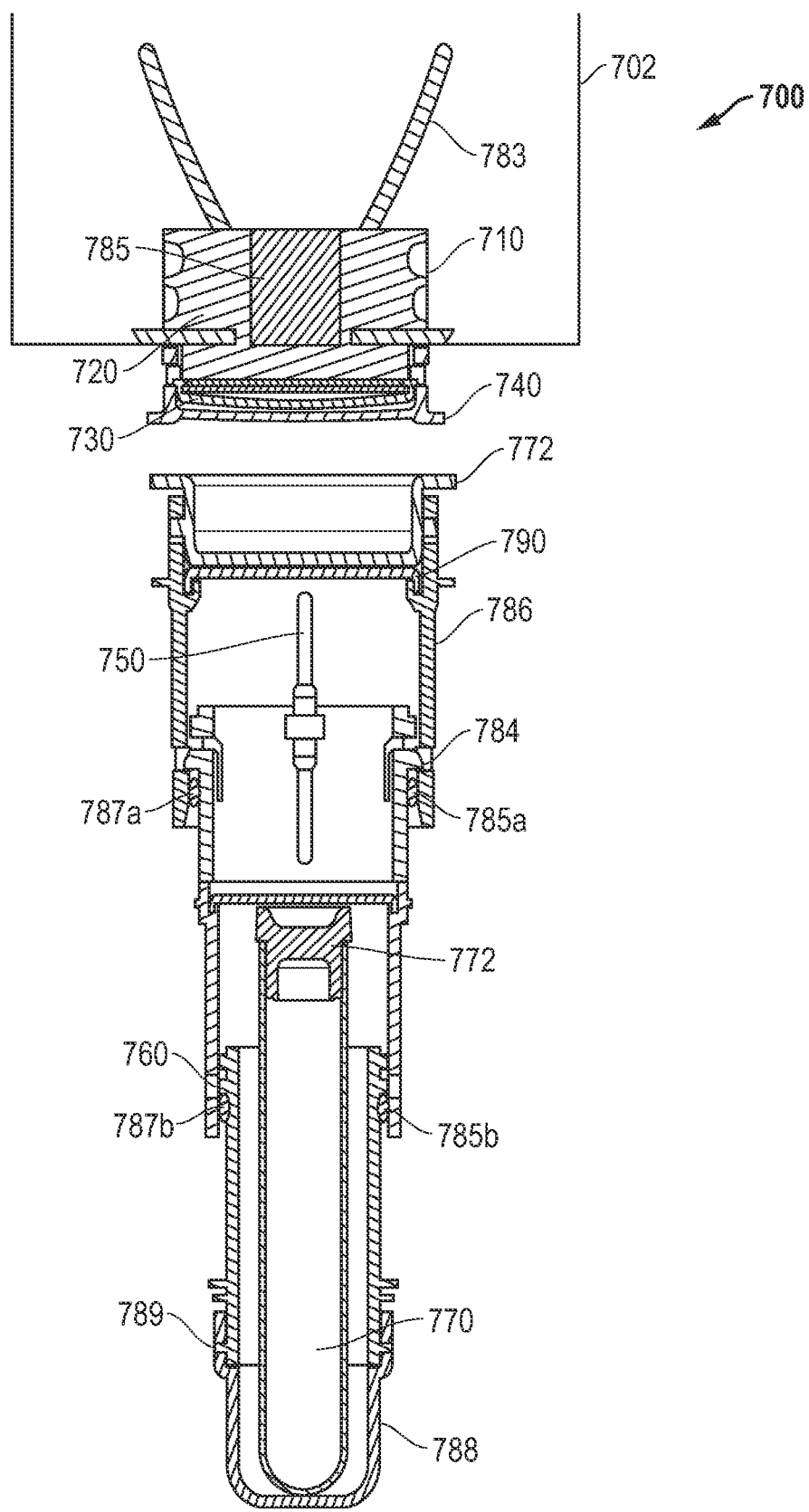
FIG. 7A illustrates a cross-sectional view of a sampling system according to a number of embodiments of the present disclosure.
Figure 7B:
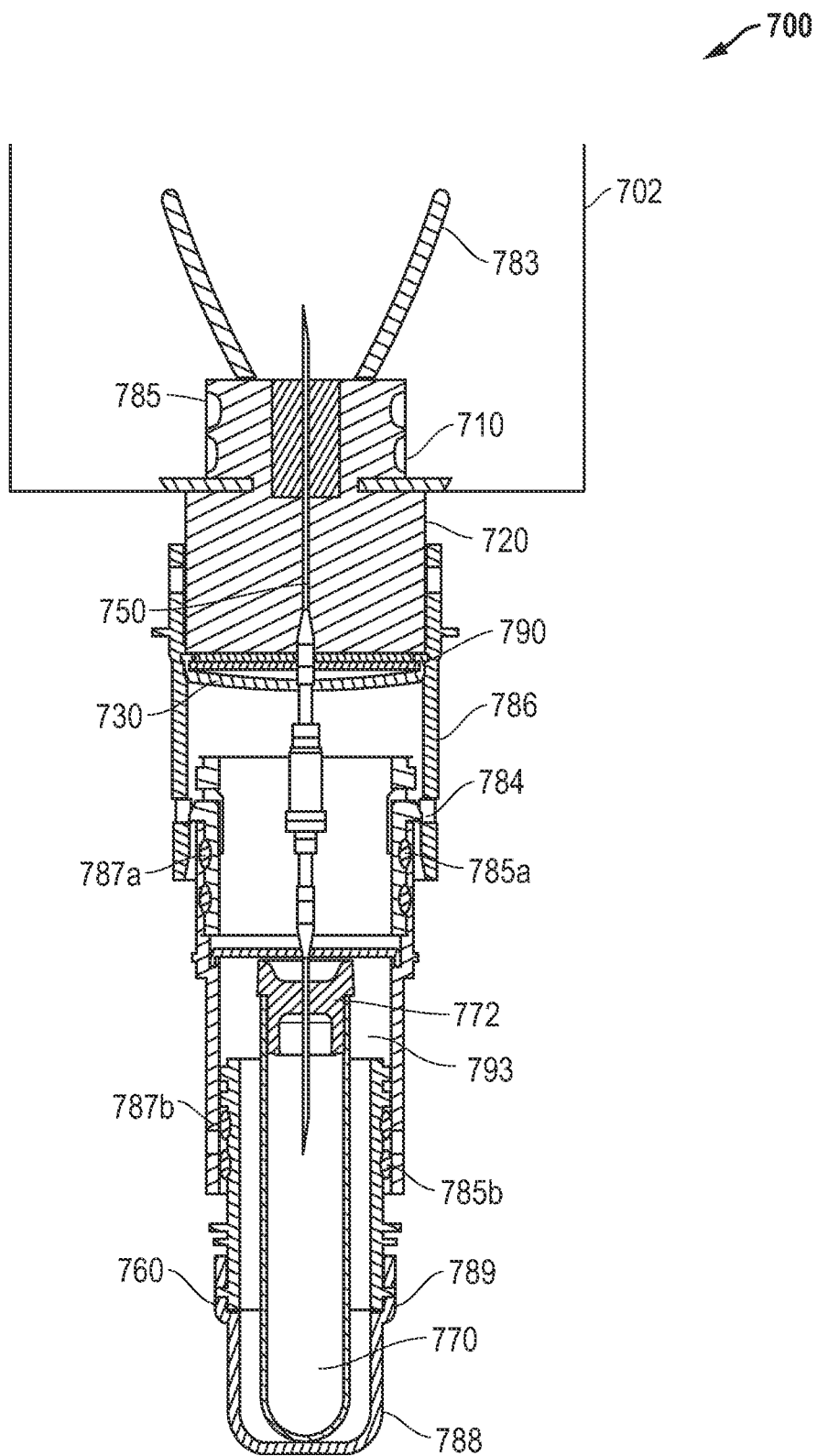
FIG. 7B illustrates a cross-sectional view of a sampling system according to a number of embodiments of the present disclosure.
Figure 7C:
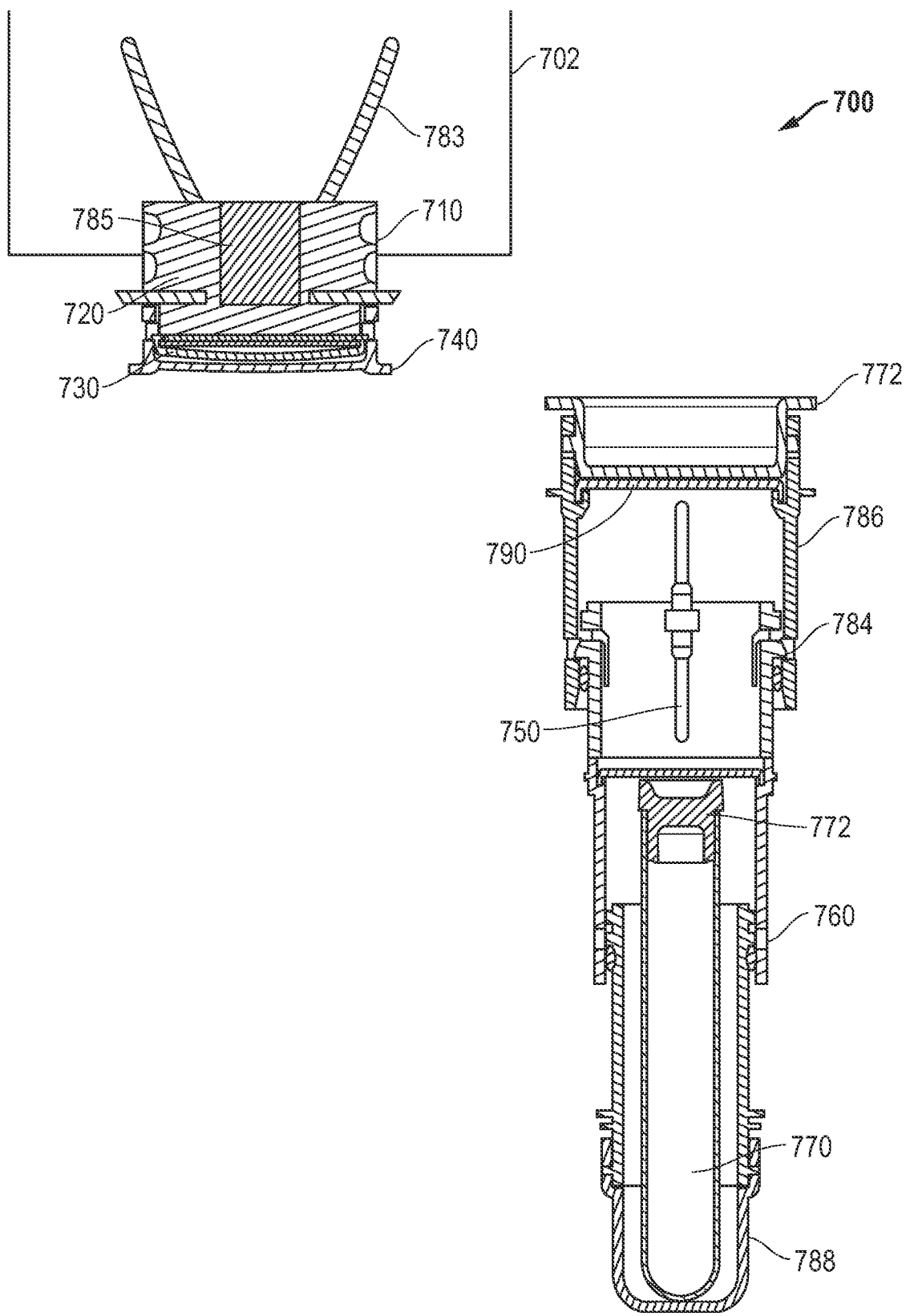
FIG. 7C illustrates a cross-sectional view of a sampling system according to a number of embodiments of the present disclosure.

FIGS. 7A-7C illustrate a cross-sectional view of a sampling system according to a number of embodiments of the present disclosure. As shown in FIGS. 7A-7C, in an alternative embodiment of the sampling system 700, the sterile dispenser assembly 710 may include the valve 720, membrane 730, needle shield 783, and septum 785 similar to the sampling system described above in FIG. 6. The sterile dispenser assembly 710 may further include a cap 740.

In an alternative embodiment of the sampling system 700, the detachable sterile sampling container assembly 760 may include a sampling container 770 with a sampling container cap 772, a membrane 790, and a sampling container housing 780 similar to the sampling system described above in FIG. 6. The detachable sterile sampling container assembly 660 may further include a cap 772. In this alternative embodiment, the sampling container housing 780 may include a top portion 786, a compressible portion 784, and a bottom portion 788. In this alternative embodiment, the compressible portion 784 may include multiple interfaces 787a, 787b with the top portion 786 and an interface 789 with the bottom portion 788. Further, the compressible portion 784 may include multiple rolling portions 785a, 785b. In a number of embodiments, the rolling portion may be an O-ring. In a number of embodiments, the double-sided needle 750 may be located in the detachable sterile sampling container assembly 660 as shown.

In operation as shown best in FIG. 7B, an upward force on the sampling system 700 forces the needle 750 through the septum 785 where it enters the vessel to draw fluid similar to the sampling system of FIG. 6. However, the interfaces 787a, 787b between the compressible portion 784 of the sampling container housing 780 may uncouple with the top portion 786 from the interface 687 and introduce the sampling container 770 to the bottom end of the needle 750 through the membranes 790 as described above while introducing the top end of the needle 750 through the membrane 730 and septum 785. As shown in this embodiment, the rolling portions 785a, 785b may allow the compressible portion 784 to slide inside the top portion 786 in use and the compressible portion 784 may fill a cavity 793 in the top portion 786 while the sampling container 770 is moving into contact with the needle 750 through an interface between the sterile dispenser assembly 710 and the sterile sampling container assembly 760 similar to the sampling system of FIG. 6 above. All other components of the sampling system may function similarly to how they function in the embodiments described above. FIG. 7C illustrates separation of the sterile dispenser assembly 710 and the sterile sampling container assembly 760 with caps 740, 772 reinstalled. In this way, fluid may be sampled from the vessel in a closed aseptic system.

In particular embodiments, at least one of the components of the sampling system (including all components of the sterile dispenser assembly, the detachable sterile sampling container assembly, or the vessel) can formed of a material including, metal, plastic, glass, or combinations thereof, and particularly Pyrex. In certain embodiments, at least one of the components of the sampling system can be formed of a material including plastic or glass. In an embodiment, at least one of the components of the sampling system may include a polymer. In an embodiment, at least one of the components of the sampling system may include a blend of polymers or polymeric polymers including a thermoplastic elastomeric hydrocarbon block copolymer, a polyether-ester block co-polymer, a thermoplastic polyamide elastomer, a thermoplastic polyurethane elastomer, a thermoplastic polyolefin elastomer, a thermoplastic vulcanizate, an olefin-based co-polymer, an olefin-based ter-polymer, a polyolefin plastomer, or combinations thereof. In an embodiment, at least one of the components of the sampling system may include a styrene-based block copolymer such as styrene-butadiene, styrene-isoprene, blends or mixtures thereof, mixtures thereof, and the like. Exemplary styrenic thermoplastic elastomers include triblock styrenic block copolymers (SBC) such as styrene-butadiene-styrene (SBS), styrene-isoprene-styrene (SIS), styrene-ethylene butylene-styrene (SEBS), styrene-ethylene propylene-styrene (SEPS), styrene-ethylene-ethylene-butadiene-styrene (SEEBS), styrene-ethylene-ethylene-propylene-styrene (SEEPS), styrene-isoprene-butadiene-styrene (SIBS), or combinations thereof. Commercial examples include some grades of Kraton™ and Hybrar™ resins.

In an embodiment, at least one of the components of the sampling system may include a polyolefin polymer. A typical polyolefin may include a homopolymer, a copolymer, a terpolymer, an alloy, or any combination thereof formed from a monomer, such as ethylene, propylene, butene, pentene, methyl pentene, hexene, octene, or any combination thereof. In an embodiment, the polyolefin polymer may be copolymers of ethylene with propylene or alpha-olefins or copolymers of polypropylene with ethylene or alpha-olefins made by metallocene or non-metallocene polymerization processes. Commercial polyolefin examples include Affinity™, Engage™, Flexomer™, Versify™, Infuse™, Exact™, Vistamaxx™, Softel™ and Tafmer™, Notio™ produced by Dow, ExxonMobil, Londel-Basell and Mitsui. In an embodiment, the polyolefin polymer may include copolymers of ethylene with polar vinyl monomers such as acetate (EVA), acrylic acid (EAA), methyl acrylate (EMA), methyl methacrylate (EMMA), ethyl acrylate (EEA) and butyl acrylate (EBA). Exemplary suppliers of these ethylene copolymer resins include DuPont, Dow Chemical, Mitusi and Arkema etc. In another embodiment, the polyolefin polymer can be a terpolymer of ethylene, maleic anhydride and acrylates such as Lotader™ made by Arkema and Evalloy™ produced by DuPont. In yet another embodiment, the polyolefin polymer can be an ionomer of ethylene and acrylic acid or methacrylic acid such as Surlyn™ made by DuPont. In an embodiment, the polyolefin is a reactor grade thermoplastic polyolefin polymer, such as P6E2A-005B available from Flint Hills Resources. In very particular embodiments, the thermoplastic tube can include a C-FLEX® brand biopharmaceutical tubing (available from Saint-Gobain Performance Plastics Corporation at Clearwater, Florida, USA. In an embodiment, at least one of the components of the sampling system may include, but are not limited to, thermoplastic, thermosets, fluropolymers, and combinations thereof. Specific examples of suitable polymer material can be polyvinylidene fluoride (PVDF). In an embodiment, at least one of the components of the sampling system can be formed of a thermoplastic elastomer, silicone, or combinations thereof. For example, specific types of thermoplastic elastomers can be those described in U.S. Patent Application Publication No. 2011/0241262, which is incorporated herein by reference, in its entirety, for all useful purposes.

In an embodiment, at least one of the components of the sampling system may include a fluorinated polymer. In an embodiment, at least one of the components of the sampling system may include a polymer including at least one of polytetrafluoroethylene (PTFE), modified polytetrafluoroethylene (mPTFE), ethylene-tetrafluoroethylene (ETFE), perfluoroalkoxyethylene (PFA), tetrafluoroethylene-hexafluoropropylene (FEP), tetrafluoro-ethylene-perfluoro (methyl vinyl ether) (MFA), polyvinylidene fluoride (PVDF), ethylene-chlorotrifluoroethylene (ECTFE), poly-imide (PI), polyamidimide (PAI), polyphenylene sulfide (PPS), polyethersulofone (PES), polyphenylene sulfone (PPSO2), liquid crystal polymers (LCP), polyetherketone (PEK), polyether ether ketones (PEEK), aromatic polyesters (Ekonol), of polyether-ether-ketone (PEEK), polyetherketone (PEK), liquid crystal polymer (LCP), polyamide (PA), polyoxymethylene (POM), polyethylene (PE)/UHMPE, polypropylene (PP), polystyrene, styrene butadiene copolymers, polyesters, polycarbonate, polyacrylonitriles, polyamides, styrenic block copolymers, ethylene vinyl alcohol copolymers, ethylene vinyl acetate copolymers, polyesters grafted with maleic anhydride, poly-vinylidene chloride, aliphatic polyketone, liquid crystalline polymers, ethylene methyl acrylate copolymer, ethylene-norbomene copolymers, polymethylpentene and ethylene acyrilic acid copoloymer, mixtures, copolymers and any combination thereof. In a specific embodiment, at least one of the components of the sampling system may include a perfluoroalkoxyalkane (PFA).

In an embodiment, at least one of the components of the sampling system may include a metal or metal alloy. In an embodiment, the metal may be aluminum, iron, tin, platinum, titanium, magnesium, alloys thereof, or maybe a different metal. Further, the metal can include steel. The steel can include stainless steel, such as austenitic stainless steel. Moreover, the steel can include stainless steel including chrome, nickel, or a combination thereof. For example, the steel can include X10CrNi18-8 stainless steel.

Further, in an embodiment, at least one of the components of the sampling system can include one or more additives. For example, the one or more additives can include a plasticizer, a catalyst, a silicone modifier, a silicon component, a stabilizer, a curing agent, a lubricant, a colorant, a filler, a blowing agent, another polymer as a minor component, or a combination thereof. In a particular embodiment, the plasticizer can include mineral oil.

In an embodiment, at least one of the components of the sampling system can be formed as a single piece or may be formed as multiple pieces. In an embodiment, at least one of the components of the sampling system can be a molded component. In an embodiment, at least one of the components of the sampling system can be formed through overmolding or other methods known in the art. In an embodiment, the polymer or polymeric blend included in at least one of the components of the sampling system may be processed by any known method to form the polymeric mixture. The polymer or polymeric blend may be melt processed by dry blending or compounding. The dry blend may be in powder, granular, or pellet form. The blend can be made by a continuous twin-screw compounding process or batch-related Banbury process. Pellets of these mixtures may then be fed into a single screw extruder to make articles such as flexible tubing products. Mixtures can also be mixed in a single-screw extruder equipped with mixing elements and then extruded directly into articles such as tubing products. In a particular embodiment, the mixture can be melt processed by any method envisioned known in the art such as laminating, casting, molding, extruding, and the like. In an embodiment, the mixture can be injection molded.

In an embodiment the polymer or polymeric blend can advantageously withstand sterilization processes. In an embodiment, the polymer or polymeric blend may be sterilized by any method envisioned. For instance, the polymer or polymeric blend is sterilized after at least one of the components of the sampling system is formed. Exemplary sterilization methods include steam, gamma, ethylene oxide, E-beam techniques, combinations thereof, and the like.

Further, the polymer or polymeric blend may be able to undergo autoclave sterilization. In a particular embodiment, the polymer or polymeric blend is sterilized by gamma irradiation. For instance, the polymer or polymeric blend of at least one of the components of the sampling system may be gamma sterilized at between about 25 kGy to about 55 kGy. In a particular embodiment, the polymer or polymeric blend is sterilized by steam sterilization. In an exemplary embodiment, the polymer or polymeric blend is heat-resistant to steam sterilization at temperatures up to about 130° C. for a time of up to about 45 minutes. In an embodiment, the polymer or polymeric blend is heat resistant to steam sterilization at temperatures of up to about 135° C. for a time of up to about 30 minutes.

In an embodiment, the polymer or polymeric blend of at least one of the components of the sampling system may be formed into a single layer article, a multi-layer article, or can be laminated, coated, or formed on a substrate to form at least one of the components of the sampling system. Multi-layer articles may include layers such as reinforcing layers, adhesive layers, barrier layers, chemically resistant layers, metal layers, any combination thereof, and the like. The polymer or polymeric blend can be formed into any useful shape such as film, sheet, tubing, and the like to form at least one of the components of the sampling system.

In embodiment, at least one of the components of the sampling system may have further desirable physical and mechanical properties. For instance, at least one of the components of the sampling system may appear transparent or at least translucent. In a specific example, the container housing of the sterile sampling container assembly is transparent or translucent. For instance, at least one of the components of the sampling system may have a light transmission greater than about 2%, or greater than about 5% in the visible light wavelength range. In particular, the resulting articles have desirable clarity or translucency. In addition, at least one of the components of the sampling system have advantageous physical properties, such as a balance of any one or more of the properties of hardness, flexibility, surface lubricity, valve life, spallation, fouling, tensile strength, elongation, Shore A hardness, gamma resistance, weld strength, and seal integrity to an optimum level.

In an embodiment, at least one of the components of the sampling system may have desirable heat stability properties. In a particular embodiment, at least one of the components of the sampling system has one more of the following heat resistance properties such as a higher burst resistance, a higher softening point, and/or a higher autoclaving temperature compared to currently available commercial products. Applications for the polymer or polymeric blend are numerous. In particular, the polymer or polymeric blend is non-toxic, making the material useful for any application where no toxicity is desired. For example, the polymer or polymeric blend may be substantially free of plasticizers or other low-molecular weight extenders that can be leached into the fluids it transfers. "Substantially free" as used herein refers to a polymeric mixture having a total organics content (TOC) (measured in accordance to ISO 15705 and EPA 410.4) of less than about 100 ppm. Further, the polymer or polymeric blend has biocompatiblity and animal derived component-free formulation ingredients. For instance, the polymeric mixture has potential for FDA, USP, EP, ISO, and other regulatory approvals. In an exemplary embodiment, the polymer or polymeric blend may be used in applications such as industrial, medical, health care, biopharmaceutical, pharmaceutical, drinking water, food & beverage, laboratory, dairy, and the like. In an embodiment, the polymeric mixture may be used in applications where low-temperature resistance is desired. In an embodiment, the polymer or polymeric blend may also be safely disposed as it generates substantially no toxic gases when incinerated and leaches no plasticizers into the environment if land filled.

Use of the sampling system may provide increased benefits in several applications in fields such as, but not limited to, industrial, medical, health care, biopharmaceutical, pharmaceutical, drinking water, food & beverage, laboratory, dairy, or other types of applications. Notably, the use of the sampling system may provide a means for accurately sampling from a fluid vessel easily at multiple sample sizes while maintaining sterility, decreasing complexity and time necessary to sample fluids from vessel. Further, the sampling system may decrease cell settling in the sampling system, providing more accurate sampling.

Many different aspects and embodiments are possible. Some of those aspects and embodiments are described below. After reading this specification, skilled artisans will appreciate that those aspects and embodiments are only illustrative and do not limit the scope of the present invention.

Embodiment 1: A sampling system for sampling a fluid from a vessel, wherein the sampling system comprises: a sterile dispenser assembly operatively connected to the vessel, the sterile dispenser assembly comprising a valve operatively connected to the vessel, a membrane, and a needle, and a detachable sterile sampling container assembly operatively connected to the sterile dispenser assembly, the detachable sterile sampling container assembly comprising a sampling container, a membrane attached to the sampling container, and a sampling container housing enclosing the sampling container, wherein the sampling container housing comprises a compressible portion having a deflated configuration and an expanded configuration, and wherein, when the compressible portion is in a deflated configuration, the compressible portion pushes the sampling container of the sterile sampling container assembly through the membrane of the sterile sampling container assembly and into proximity with the needle, allowing the needle to dispense the fluid into the sampling container while maintaining a closed aseptic system.

Embodiment 2: A sampling system for sampling a fluid from a vessel, wherein the sampling system comprises: a sterile dispenser assembly operatively connected to the vessel, the sterile dispenser assembly comprising a valve, a membrane, and a needle, wherein the valve comprises a valve body and a valve stem disposed at least partially within the valve body, the valve stem comprising a sidewall defining a central lumen and at least one opening in the sidewall, wherein the valve is adapted to prevent fluid flow through the lumen when the at least one opening is disposed within the valve body and permit fluid flow through the lumen when the at least one opening is exposed from the valve body, wherein the valve is essentially free of a spring, and wherein the needle is operatively connected to the valve to dispense fluid from the vessel.

Embodiment 3: A sampling system for sampling a fluid from a vessel, wherein the sampling system comprises: a detachable sterile sampling container assembly comprising a sampling container, a membrane attached to the sampling container, and a sampling container housing enclosing the sampling container, wherein the sampling container housing comprises a compressible portion having a deflated configuration and an expanded configuration, and wherein, when the compressible portion is in a deflated configuration, the compressible portion pushes the sampling container through the membrane into proximity with a needle, allowing the needle to dispense the fluid into the sampling container while maintaining a closed aseptic system.

Embodiment 4: A method for sampling a fluid from a vessel, comprising: providing a vessel comprising a fluid; operatively connecting a sterile dispenser assembly to the vessel, the sterile dispenser assembly comprising a valve, a membrane, and a needle; operatively connecting a detachable sterile sampling container assembly to the sterile sampling container assembly, the detachable sterile sampling container assembly comprising a sampling container, a membrane attached to the sampling container, and a sampling container housing comprising a compressible portion enclosing the sampling container; and deflating the compressible portion of the sampling container housing to push the sampling container of the sterile sampling container assembly through the membrane of the sterile sampling container assembly and into proximity with the needle, allowing the needle to dispense the fluid into the sampling container while maintaining a closed aseptic system.

Embodiment 5: The sampling system or method of any of the preceding embodiments, wherein the fluid comprises a biological media comprising cells.

Embodiment 6: The sampling system or method of any of the preceding embodiments, wherein the vessel comprises a cell culture container.

Embodiment 7: The sampling system or method of any of embodiments 1 and 3-6, wherein the membrane of the sterile sampling container assembly comprises a breathable valve membrane.

Embodiment 8: The sampling system or method of any of embodiments 1-2 and 4-7, wherein the membrane of the sterile dispenser assembly comprises a breathable valve membrane.

Embodiment 9: The sampling system or method of any of embodiments 7-8, wherein the breathable valve membrane comprises a silicone.

Embodiment 10: The sampling system or method of any of the preceding embodiments, wherein the sampling system comprises a plurality of sterile dispenser assemblies operatively connected to the vessel.

Embodiment 11: The sampling system or method of any of the preceding embodiments, wherein the sampling system is capable of undergoing autoclave sterilization, ethylene oxide sterilization, or gamma sterilization.

Embodiment 12: The sampling system or method of any of embodiments 1 and 3-11, wherein the container housing comprises a transparent or translucent material.

Embodiment 13: The sampling system or method of any of embodiments 1 and 3-12, further comprising a disposable cap overlying at least one of the membrane or sampling container housing.

Embodiment 14: The sampling system or method of any of embodiments 1 and 3-13, wherein the sampling container housing comprises a top portion disposed above the compressible portion and a bottom portion disposed below the compressible portion.

Embodiment 15: The sampling system or method of embodiment 14, wherein at least one of the top portion or the bottom portion is detachable from the compressible portion.

Embodiment 16: The sampling system or method of any of embodiments 1-2 and 4-13, further comprising a disposable cap overlying at least one of the membrane or valve of the sterile dispenser assembly.

Embodiment 17: The sampling system or method of any of the preceding embodiments, wherein the needle comprises a needle sleeve.

Embodiment 18: The sampling system of embodiment 3, wherein the sterile sampling container assembly further comprises a needle operatively connected to the membrane or sampling container housing.

Embodiment 19: The sampling system or method of any of the preceding embodiments, wherein the compressible portion comprise an elastomer.

Embodiment 20: The sampling system or method of any of the preceding embodiments, wherein the sampling container comprises a sampling container cap.

Embodiment 21: The sampling system or method of any of the preceding embodiments, wherein the sterile valve of the sterile dispenser assembly exhibits a cell density, MSC, of between XX and YY cell/cm$^2$.

Embodiment 22: The method of any of embodiments 4-21, further comprising, removing the sampling container from the sample container housing of the sampling container assembly.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

Note that not all of the activities described above in the general description or the examples are required, that a portion of a specific activity may not be required, and that one or more further activities may be performed in addition to those described. Still further, the order in which activities are listed are not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed:

1. A sampling system for sampling a fluid from a vessel, wherein the sampling system comprises:
    a sterile dispenser assembly operatively connected to the vessel, the sterile dispenser assembly comprising a valve operatively connected to the vessel, a membrane, and a needle, and
    a detachable sterile sampling container assembly operatively connected to the sterile dispenser assembly, the detachable sterile sampling container assembly comprising a sampling container, a membrane attached to the sampling container, and a sampling container housing enclosing the sampling container,
        wherein the sampling container housing comprises a compressible portion having a deflated configuration and an expanded configuration, and
        wherein, when the compressible portion is in a deflated configuration, the compressible portion pushes the sampling container of the sterile sampling container assembly through the membrane of the sterile sampling container assembly and into proximity with the needle, allowing the needle to dispense the fluid into the sampling container while maintaining a closed aseptic system.

2. The sampling system of claim 1, wherein the fluid comprises a biological media comprising cells.

3. The sampling system of claim 1, wherein the vessel comprises a cell culture container.

4. The sampling system of claim 1, wherein the membrane of the sterile sampling container assembly comprises a breathable valve membrane.

5. The sampling system of claim 1, wherein the membrane of the sterile dispenser assembly comprises a breathable valve membrane.

6. The sampling system of claim 5, wherein the breathable valve membrane comprises a silicone.

7. The sampling system of claim 1, wherein the sampling system comprises a plurality of sterile dispenser assemblies operatively connected to the vessel.

8. The sampling system of claim 1, wherein the sampling system is capable of undergoing autoclave sterilization, ethylene oxide sterilization, or gamma sterilization.

9. The sampling system of claim 1, wherein the container housing comprises a transparent or translucent material.

10. The sampling system of claim 1, further comprising a disposable cap overlying at least one of the membrane or sampling container housing.

11. The sampling system of claim 1, wherein the sampling container housing comprises a top portion disposed above the compressible portion and a bottom portion disposed below the compressible portion.

12. The sampling system of claim 11, wherein at least one of the top portion or the bottom portion is detachable from the compressible portion.

13. The sampling system of claim 1, further comprising a disposable cap overlying at least one of the membrane or valve of the sterile dispenser assembly.

14. The sampling system of claim 1, wherein the needle comprises a needle sleeve.

15. The sampling system of claim 1, wherein the compressible portion comprises an elastomer.

16. The sampling system of claim 1, wherein the sampling container comprises a sampling container cap.

17. A sampling system for sampling a fluid from a vessel, wherein the sampling system comprises:
    a sterile dispenser assembly operatively connected to the vessel, the sterile dispenser assembly comprising a valve, a membrane, and a needle, wherein the valve comprises a valve body and a valve stem disposed at least partially within the valve body, the valve stem comprising a sidewall defining a central lumen and at least one opening in the sidewall, wherein the valve is adapted to prevent fluid flow through the lumen when the at least one opening is disposed within the valve body and permit fluid flow through the lumen when the at least one opening is exposed from the valve body, wherein the valve is essentially free of a spring, and wherein the needle is operatively connected to the valve to dispense fluid from the vessel.

18. A sampling system for sampling a fluid from a vessel, wherein the sampling system comprises:
    a detachable sterile sampling container assembly comprising a sampling container, a membrane attached to the sampling container, and a sampling container housing enclosing the sampling container,
        wherein the sampling container housing comprises a compressible portion having a deflated configuration and an expanded configuration, and
        wherein, when the compressible portion is in a deflated configuration, the compressible portion pushes the sampling container through the membrane into proximity with a needle, allowing the needle to dispense the fluid into the sampling container while maintaining a closed aseptic system.

19. The sampling system of claim 18, wherein the sterile sampling container assembly further comprises a needle operatively connected to the membrane or sampling container housing.

* * * * *